(12) United States Patent
Vandyck et al.

(10) Patent No.: US 10,160,743 B2
(45) Date of Patent: Dec. 25, 2018

(54) SULPHAMOYLTHIOPHENAMIDE DERIVATIVES AND THE USE THEREOF AS MEDICAMENTS FOR THE TREATMENT OF HEPATITIS B

(71) Applicant: Janssen Sciences Ireland UC, Co Cork (IE)

(72) Inventors: Koen Vandyck, Paal-Beringen (BE); Geerwin Yvonne Paul Haché, Kapellen (BE); Stefaan Julien Last, Lint (BE); Wim Gaston Verschueren, Berchem (BE); Pierre Jean-Marie Bernard Raboisson, Rosieres (BE)

(73) Assignee: JANSSEN SCIENCES IRELAND UC, Little Island, Co Cork (IE)

( * ) Notice: Subject to any disclaimer, the term of this patent is extended or adjusted under 35 U.S.C. 154(b) by 0 days.

(21) Appl. No.: 14/891,895

(22) PCT Filed: May 16, 2014

(86) PCT No.: PCT/EP2014/060132
§ 371 (c)(1),
(2) Date: Nov. 17, 2015

(87) PCT Pub. No.: WO2014/184365
PCT Pub. Date: Nov. 20, 2014

(65) Prior Publication Data
US 2016/0115149 A1    Apr. 28, 2016

(30) Foreign Application Priority Data

| May 17, 2013 | (EP) | 13168295 |
| Sep. 19, 2013 | (EP) | 13185227 |
| Mar. 5, 2014 | (EP) | 14157917 |

(51) Int. Cl.
C07D 333/38    (2006.01)
C07D 409/12    (2006.01)

(52) U.S. Cl.
CPC ......... *C07D 333/38* (2013.01); *C07D 409/12* (2013.01)

(58) Field of Classification Search
USPC ........................................ 514/444, 445, 470
See application file for complete search history.

(56) References Cited

U.S. PATENT DOCUMENTS

| 3,843,662 A | 10/1974 | Holland et al. |
| 4,569,940 A | 2/1986 | Watts et al. |
| 4,962,101 A | 10/1990 | DiNinno et al. |
| 4,995,898 A | 2/1991 | Nasu et al. |
| 5,272,167 A | 12/1993 | Girijavallabhan et al. |
| 5,308,826 A | 5/1994 | Chin et al. |
| 5,314,880 A | 5/1994 | Whittaker et al. |
| 5,571,821 A | 11/1996 | Chan et al. |
| 5,585,327 A | 12/1996 | Chin et al. |
| 5,607,929 A | 3/1997 | Nicol et al. |
| 5,708,034 A | 1/1998 | Kleemann et al. |
| 5,723,411 A | 3/1998 | Stevenson et al. |
| 5,756,524 A | 5/1998 | Riordan et al. |
| 5,795,907 A | 8/1998 | Kalindjian et al. |
| 5,912,260 A | 6/1999 | Kalindjian et al. |
| 5,919,970 A | 7/1999 | Song et al. |
| 5,939,423 A | 8/1999 | Karlin et al. |
| 6,025,367 A | 2/2000 | Forbes et al. |
| 6,265,408 B1 | 7/2001 | Forbes et al. |
| 6,476,025 B1 | 11/2002 | Gutterer |
| 6,650,463 B2 | 11/2003 | Obikawa et al. |
| 6,668,527 B2 | 12/2003 | Chupak et al. |
| 6,780,389 B2 | 8/2004 | Karl et al. |
| 7,115,595 B2 | 10/2006 | Sunagawa et al. |
| 7,186,735 B2 | 3/2007 | Strobel et al. |
| 7,338,956 B2 | 3/2008 | Strobel et al. |
| 7,368,457 B2 | 5/2008 | Josien et al. |
| 7,384,967 B2 | 6/2008 | Polisetti et al. |
| 7,476,688 B2 | 1/2009 | Suzuki et al. |
| 7,541,373 B2 | 6/2009 | Polisetti et al. |
| 7,544,700 B2 | 6/2009 | Halazy et al. |
| 7,595,322 B2 | 9/2009 | Morgan et al. |
| 7,608,723 B2 | 10/2009 | Boyce et al. |
| 7,750,158 B2 | 7/2010 | Shankar et al. |
| 7,786,104 B2 | 8/2010 | DuBois et al. |

(Continued)

FOREIGN PATENT DOCUMENTS

| CA | 2950807 A1 | 12/2013 |
| CN | 101039919 A | 9/2007 |

(Continued)

OTHER PUBLICATIONS

AsInEx; Chemical library; Registry No. 919040-37-2; Feb. 2, 2007.*

(Continued)

*Primary Examiner* — Pancham Bakshi

(57) ABSTRACT

Inhibitors of HBV replication of formula (I)

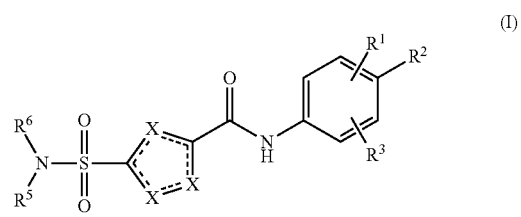

including stereochemically isomeric forms, and salts, hydrates, solvates thereof, wherein X and $R^1$ to $R^8$ have the meaning as defined herein.

The present invention also relates to processes for preparing said compounds, pharmaceutical compositions containing them and their use, alone or in combination with other HBV inhibitors, in HBV therapy.

16 Claims, No Drawings

(56) References Cited

U.S. PATENT DOCUMENTS

| | | |
|---|---|---|
| 7,790,726 B2 | 9/2010 | Zhang et al. |
| 7,838,525 B2 | 11/2010 | Jones et al. |
| 7,888,373 B2 | 2/2011 | Morgan et al. |
| 7,994,168 B2 | 8/2011 | Lennig et al. |
| 8,071,779 B2 | 12/2011 | Lampe et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,650 B2 | 4/2012 | Dubois et al. |
| 8,153,803 B2 | 4/2012 | Kazantsev et al. |
| 8,207,195 B2 | 6/2012 | Navratil et al. |
| 8,227,489 B2 | 7/2012 | Dubois et al. |
| 8,273,754 B2 | 9/2012 | Hill et al. |
| 8,299,096 B2 | 10/2012 | Navratil et al. |
| 8,299,114 B2 | 10/2012 | Dubois et al. |
| 8,354,425 B2 | 1/2013 | Dubois et al. |
| 8,394,820 B2 | 3/2013 | Dubois et al. |
| 8,399,491 B2 | 3/2013 | Dubois et al. |
| 8,404,747 B2 | 3/2013 | Kazantsev et al. |
| 8,410,147 B2 | 4/2013 | Peterson et al. |
| 8,536,168 B2 | 9/2013 | Dai et al. |
| 8,609,668 B2 | 12/2013 | Cuconati et al. |
| 8,629,274 B2 | 1/2014 | Hartman et al. |
| 8,808,702 B2 | 8/2014 | Reddy et al. |
| 8,889,716 B2 | 11/2014 | Prime et al. |
| 8,993,771 B2 | 3/2015 | Hartman et al. |
| 9,051,296 B2 | 6/2015 | Yamagishi et al. |
| 9,061,008 B2 | 6/2015 | Hartman et al. |
| 9,066,932 B2 | 6/2015 | Hartman et al. |
| 9,115,101 B2 | 8/2015 | Bodil Van Niel et al. |
| RE45,670 E | 9/2015 | Polisetti et al. |
| 9,156,839 B2 | 10/2015 | Vandyck et al. |
| 9,169,212 B2 | 10/2015 | Hartman et al. |
| 9,181,288 B2 | 11/2015 | Hartman et al. |
| 9,205,079 B2 | 12/2015 | Hartman |
| 9,339,510 B2 | 5/2016 | Hartman et al. |
| 9,400,280 B2 | 7/2016 | Hartman |
| 9,458,176 B2 | 10/2016 | Takaishi et al. |
| 9,505,722 B2 | 11/2016 | Hartman et al. |
| 9,567,299 B2 | 2/2017 | Vandyck et al. |
| 9,579,313 B2 | 2/2017 | Hartman |
| 9,676,747 B2 | 6/2017 | Hartman et al. |
| 2002/0049236 A1 | 4/2002 | Chupak et al. |
| 2003/0114443 A1 | 6/2003 | Imamura et al. |
| 2004/0039009 A1 | 2/2004 | Jagtap et al. |
| 2004/0110802 A1 | 6/2004 | Thorarensen et al. |
| 2005/0009871 A1 | 1/2005 | Ramesh et al. |
| 2005/0054850 A1 | 3/2005 | Wu et al. |
| 2005/0129833 A1 | 6/2005 | Kincaid et al. |
| 2005/0148632 A1 | 7/2005 | Tokumasu et al. |
| 2005/0221272 A1 | 10/2005 | Housman et al. |
| 2005/0239833 A1 | 10/2005 | Kazantsev et al. |
| 2006/0040984 A1 | 2/2006 | Luckhurst et al. |
| 2006/0100228 A1 | 5/2006 | Shankar et al. |
| 2006/0100257 A1 | 5/2006 | Muto |
| 2006/0122236 A1 | 6/2006 | Wood et al. |
| 2007/0142440 A1 | 6/2007 | Burgdorf et al. |
| 2007/0161578 A1 | 7/2007 | Hwa et al. |
| 2009/0018118 A1 | 1/2009 | Urleb et al. |
| 2009/0036420 A1 | 2/2009 | Galley et al. |
| 2009/0105218 A1 | 4/2009 | Ulven et al. |
| 2009/0163545 A1 | 6/2009 | Goldfarb et al. |
| 2009/0259044 A1 | 10/2009 | Kazantsev et al. |
| 2009/0325959 A1 | 12/2009 | Vittitow et al. |
| 2009/0325960 A1 | 12/2009 | Fulcher et al. |
| 2010/0008968 A1 | 1/2010 | Lampe et al. |
| 2010/0016310 A1 | 1/2010 | Ingraham |
| 2010/0022517 A1 | 1/2010 | Richards et al. |
| 2010/0087415 A1 | 4/2010 | Whitten et al. |
| 2010/0204210 A1 | 8/2010 | Sorensen et al. |
| 2011/0009622 A1 | 1/2011 | Jitsuoka et al. |
| 2011/0064695 A1 | 3/2011 | Qiu et al. |
| 2011/0064696 A1 | 3/2011 | Or et al. |
| 2011/0065686 A1 | 3/2011 | Mazola Reyes et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2011/0301158 A1 | 12/2011 | Polisetti et al. |
| 2013/0005756 A1 | 1/2013 | Navratil et al. |
| 2013/0131059 A1 | 5/2013 | Lampe et al. |
| 2013/0131106 A1 | 5/2013 | Lampe et al. |
| 2013/0142827 A1 | 6/2013 | Block et al. |
| 2013/0203733 A1 | 8/2013 | Kazantsev et al. |
| 2013/0251673 A1 | 9/2013 | Hartman et al. |
| 2013/0267517 A1 | 10/2013 | Guo et al. |
| 2013/0303552 A1 | 11/2013 | Xu et al. |
| 2014/0178337 A1 | 6/2014 | Hartman et al. |
| 2014/0179665 A1 | 6/2014 | Hartman et al. |
| 2014/0275167 A1 | 9/2014 | Hartman |
| 2015/0152073 A1 | 6/2015 | Hartman et al. |
| 2015/0174115 A1 | 6/2015 | Hartman et al. |
| 2015/0175602 A1 | 6/2015 | Brown et al. |
| 2015/0197493 A1 | 7/2015 | Hartman |
| 2015/0197533 A1 | 7/2015 | Hartman et al. |
| 2015/0216938 A1 | 8/2015 | Hartman et al. |
| 2015/0225355 A1 | 8/2015 | Hartman et al. |
| 2015/0252057 A1 | 9/2015 | Guo et al. |
| 2015/0259324 A1 | 9/2015 | Hartman et al. |
| 2015/0266890 A1 | 9/2015 | Vandyck et al. |
| 2015/0274652 A1 | 10/2015 | Hartman |
| 2015/0274653 A1* | 10/2015 | Vandyck ............... C07D 205/04 514/210.19 |
| 2016/0000812 A1 | 1/2016 | Hartman et al. |
| 2016/0002155 A1 | 1/2016 | Vandyck et al. |
| 2016/0051512 A1 | 2/2016 | Vandyck et al. |
| 2016/0083383 A1 | 3/2016 | Guo et al. |
| 2016/0115125 A1 | 4/2016 | Vandyck et al. |
| 2016/0115149 A1 | 4/2016 | Vandyck et al. |
| 2016/0158214 A1 | 6/2016 | Hartman |
| 2016/0176817 A1 | 6/2016 | Vandyck et al. |
| 2016/0272599 A1 | 9/2016 | Hartman et al. |
| 2016/0347741 A1 | 12/2016 | Vandyck et al. |
| 2017/0002025 A1 | 1/2017 | Vendeville et al. |
| 2017/0015629 A1 | 1/2017 | Hartman et al. |
| 2017/0114018 A1 | 4/2017 | Hartman |
| 2017/0158634 A1 | 6/2017 | Vandyck et al. |
| 2017/0182021 A1 | 6/2017 | Hartman |
| 2017/0334882 A1 | 11/2017 | Hartman et al. |

FOREIGN PATENT DOCUMENTS

| | | |
|---|---|---|
| CN | 102206172 A | 10/2011 |
| JP | 62142164 | 6/1987 |
| WO | 199207835 A1 | 5/1992 |
| WO | 199909022 A1 | 2/1999 |
| WO | 2003002518 A1 | 1/2003 |
| WO | WO 2005/115374 A | 12/2005 |
| WO | 2006102642 A2 | 2/2006 |
| WO | 2007070556 A2 | 6/2007 |
| WO | 2008154819 A1 | 12/2008 |
| WO | 2009018219 A2 | 2/2009 |
| WO | 2010059658 A1 | 5/2010 |
| WO | WO 2010/123139 A | 10/2010 |
| WO | WO 2010/123139 A1 | 10/2010 |
| WO | 2011140324 A1 | 11/2011 |
| WO | WO 2013/006394 A | 1/2013 |
| WO | WO 2013/006394 A1 | 1/2013 |
| WO | WO 2013/096744 A1 | 6/2013 |
| WO | 2013144129 A1 | 10/2013 |
| WO | 2013174962 | 11/2013 |
| WO | 2013184757 A1 | 12/2013 |
| WO | WO 2014/033170 A1 | 3/2014 |
| WO | WO 2014/033176 A1 | 3/2014 |
| WO | 2014161888 A1 | 10/2014 |
| WO | 2014165128 A2 | 10/2014 |
| WO | 2014184328 A1 | 11/2014 |
| WO | 2014184350 A1 | 11/2014 |
| WO | 2014184365 A1 | 11/2014 |
| WO | 2014191301 A1 | 12/2014 |
| WO | 2014191726 A1 | 12/2014 |
| WO | 2015011281 A1 | 1/2015 |
| WO | 2015057945 A1 | 4/2015 |
| WO | 2015059212 A1 | 4/2015 |

(56) References Cited

FOREIGN PATENT DOCUMENTS

| WO | 2015073774 A1 | 5/2015 |
|---|---|---|
| WO | 2015109130 A1 | 7/2015 |
| WO | 2015118057 A1 | 8/2015 |
| WO | 2015132276 A1 | 9/2015 |
| WO | 2015138895 A1 | 9/2015 |
| WO | 2015144093 A1 | 10/2015 |
| WO | 2015180631 A1 | 12/2015 |
| WO | 2016089990 A1 | 6/2016 |
| WO | 2016109663 A2 | 7/2016 |
| WO | 2016109684 A2 | 7/2016 |
| WO | 2016109689 A1 | 7/2016 |
| WO | 2016149581 A1 | 9/2016 |
| WO | 2016113273 A1 | 10/2016 |
| WO | 2016161268 A1 | 10/2016 |
| WO | 2016168619 A1 | 10/2016 |
| WO | 2016183266 A1 | 11/2016 |

OTHER PUBLICATIONS

Weber, O., et al., "Inhibition of Human Hepatitis B Virus HBV) by a Novel Non-Nucleosidic Compound in a Transgenic Mouse Model", Antiviral Research, vol. 54 p. 69-78 (2002).
International search report dated Jun. 16, 2014, for corresponding PCT/EP2014/060132 application.
U.S. Appl. No. 61/578,716, filed Dec. 21, 2011, Hartman et al.
ASLNEX; Chemical Library; Registry No. 919040-37-2; 0210212007.
El-Sayed, "A Comparative Study of the Reactions of Thiophene-2-Carboxanilides and Related Compounds", Chemistry of Heterocyclic Compounds, Springer New York LLC, US, vol. 34, No. 7, Jan. 1, 1998, pp. 796-801 (XP000881506.
Schroder et al, "Arzneimittelchemie Passage", Arzneimittelchemie Grundlagen Nerven, Muskeln Und Gewebe, XX, XX, Jan. 1, 1976, pp. 30-33 (XP002186820).
Weber, 0., et al., "Inhibition of Human Hepatitis B Virus (HBV) by a Novel Non-Nucleosidic Compound in a Transgenic Mouse Model", Antiviral Research 2002 vol. 43, pp. 69-78.
File History of U.S. Pat. No. 8, Sep. 10, 2013.
File History of U.S. Pat. No. 8,629,274.
File History of U.S. Pat. No. 9,061,008.
File History of U.S. Pat. No. 9,066,932.
U.S. Appl. No. 14/642,393, filed Mar. 9, 2015 (80 Pages).
U.S. Appl. No. 14/597,814, filed Jan. 15, 2015 (293 Pages).
Extended European Search Report dated Sep. 23, 2013 for Corresponding European Application No. EP13162131.0.
Extended European Search Report dated Jul. 8, 2013 for Corresponding European Application No. EP13168291.6.
Online Registry Via STN Dec. 22, 2008, RN 1088200-12-7.
Online Registry Via STN, Mar. 2, 2007, RN 924514-21-6.
Online Registry Via STN, Sep. 2, 2003, RN 577752-12-6.
Berke, et al., "Capsid Assembly Modulator JNJ-56136379 Prevents de Novo Infection of Primary Human Hepatocytes with Hepatitis B Virus", Hepatology, Oct. 2016, pp. 124A, 234.
Brahmania, et al., "New Therapeutic Agents for Chronic Hepatitis B", Lancet Infec Dis, vol. 16: pp. e10-21 (Feb. 2016).
Brezillon, et al., "Antiviral Activity of Bay 41-4109 on Hepatitis B Virus in Humanized Alb-uPA/SCID Mice", PLos One, vol. 6 (12): pp. e25096 (1-6) (Dec. 2011).
Chang, et al., "NMR-spectroscopy-based Metabonomic Approach to the Analysis of Bay41-4109, a novel anti-HBV Compound, induced Hepatotoxicity in Rats", Toxicology Letters, vol. 173: pp. 161-167 (2007).
Cheng-An Geng et al, Small-Molecule Inhibitors for the Treatment of Hepatitis B Virus Documented in Patents, Mini-Reviews in Medicinal Chemistry, Apr. 1, 2013, pp. 749-776 (XP055105561-XP009176654), vol. 13.
Cho, et al., "2-Amino-N-(2,6-dichloropyridin-3-yl)acetamide derivatives as a novel class of HBV capsid assembly inhibitor", Journal of Viral Hepatitis, vol. 21: pp. 843-852 (2014).

Cowie, et al., "Mortality due to viral hepatitis in the Global Burden of Disease Study 2010: new evidence of an urgent global public health priority demanding action", Antiviral Therapy,vol. 18: pp. 953-954 (2013).
Delaney, et al., "Phenylpropenamide Derivatives AT-61 and AT-130 Inhibit Replication of Wild-Tpe and Lamivudine-Resistant Strains of Hepatitis B Virus in Vitro", Antimicrobial Agents and Chemotherapy, vol. 46(9): pp. 3057-3060 (Sep. 2002).
Deres, et al., "Inhibition of Hepatitis B Virus Replication by Drug-Induced Depletion of Nucleocpsids", Science, vol. 299: pp. 893-896 (Feb. 7, 2003).
Foley, "An Effecient Synthesis of 2-Chloro-3-carboethoxy or 2-Chloro-3-cyano- 4,5-disubstituted and 5-substituted Pyrroles", Tetrahedron Letters, vol. 35(33): pp. 5989-5992, (1994).
Gane, et al., "Phase 1a Safety and Pharmacokinetics of NVR3-778, a Potential First-in-class HBV Core Inhibitor", The Abstract of the Liver Meeting 2014 (AASLD), Abstract LB-19, Boston, MA (2014).
Goodman, et al, "Discovery of potent, selective sulfonylfuran urea endothelial lipase inhibitors", Bioorganic & Medicinal Chemistry Letters, vol. 19:pp. 27-30 (2009).
Guo, et al., "HBc binds to the CpG island of HBV cccDNA and promotes an epigenetic permissive state", Epigenetics, vol. 6 (6): pp. 720-726 (Jun. 2011).
Huang, et al., "Blockage of HBV Virus Replication and Inhibition of cccDNA Establishment by Core Protein Allosteric Modifiers (CpAMs)", Hepatology, vol. 64 (1 Suppl): pp. 937A-938A, ( Oct. 2016).
Hughes, et al., "Hepatitis Delta Virus", The Lancet, vol. 378: pp. 73-85, (Jul. 2, 2011).
Jayathilaka, et al, "A chemical compound that stimulated the human homologous recombination protein RAD51", Proceedings of the National Academy of Sciences on the United States of America, vol. 105 (41): pp. 15848-15853 (Oct. 14, 2008).
Katen, et al., "Assembly-Directed Antivirals Differentially Bind Quasiequivalend Pockets to Modify Hepatitis B Virus Capsid Tertiary and Quaternary Structure", Structure, vol. 21: pp. 1406-1416 (Aug. 6, 2013).
Klumpp, et al., "High Antiviral Activity of the HBV Core Inhibitor NVR 3-778 in the Humanized UPA/SCID Mouse Model", Journal of Hepatology, vol. 62:p. S235 (2015).
Klumpp, et al., "High-resolution crystal structure of a hepatitis B virus replication inhibitor bound to the viral core protein", PNAS, vol. 112(49): pp. 15196-15201 (Dec. 8, 2015).
Lam, et al., "HBV Corre Assembly Modulators Block Antigen Prouction When Present During Infection, but not during Persistent Infection", The Abstracts of the Liver Meeting 2016 (AASLD), vol. 64 (1 Suppl.), Boston, MA (Oct. 2016).
Lam, et al., "Inhibition of Hepatitis B Virus Replication by the HBV Core Inhibitors NVR3-778", The Abstract of the Liver Meeting 2015 (AASLD), Abstract 33: p. 223A, San Francisco, CA (Oct. 2015).
Lam, et al., "Serum HBV RNA as a Pharmacodynamic (PD) Marker of HBV Treatment Response to Core Assembly Modulator NVR 3-778 and Pegylate-Interferon Alpha", Poster Presented in the AASLD/EASL—HBV Treatment Endpoints Workshop, Poster No. 3774, Alexandria, VA (Sep. 9, 2016).
Li Bing, et al., Progress in anti Hepatitus B Virus non-nucleosidic drugs, J. Liaoning Medical University, vol. 30(1): pp. 88-91 (Dec. 31, 2009.
Lucifora, et al., "Specific and Nonhepatotoxic Degradation of Nuclear Hepatitis B Virus cccDNA", Science, vol. 343: pp. 1221-1228 (Mar. 14, 2014).
Manzoor, et al, "Hepatitis B Virus Therapy: What's the future holding for us?", World Journal of Gastroenterology, vol. 21(44): pp. 12558-12575 (Nov. 28, 2015).
Marcellin, et al., "Peginterferon Alfa-2a Alone, Lamivudine Alone, and the Two in Combination in Patients with HBeAg-Negative Chronic Hepatitis B", The New England Journal of Medicine, vol. 351(12): pp. 1206-1217 (Sep. 16, 2014).
Online Registry Via STN Aug. 6, 2012. RN 1386725-02-5.
Online Registry Via STN Jun. 7, 2012, RN 1375909-37-7.
Online Registry Via STN Oct. 10, 2001, RN 361373-90-2.
Online Registry Via STN Aug. 13, 2012, RN 1390500-09-0.

(56) References Cited

OTHER PUBLICATIONS

Online Registry Via STN Jan. 16, 2001, RN 314043-17-9.
Online Registry Via STN 2010, RN 1253220-91-5.
Online Registry Via STN Aug. 30, 2011, RN 1325664-90-1.
Online Registry Via STN, Jan. 9, 2001, RN 313253-89-3.
Online Registry Via STN, Feb. 15, 2007, RN 921179-95-5.
Online Registry Via STN, Mar. 17, 2003, RN 499189-09-2.
Online Registry Via STN, Apr. 24, 2002, RN 406926-60-1.
Qiu, et al, "Antihepatitis B therapy: a review of current medications and novel small molecule inhibitors", Fudamental & Clinical Pharmacology, pp. 1-18 (XP055105340) (Nov. 1, 2013).
Qiu, et al., "Design and Synthesis of Orally Bioavailable 4-Methyl Heteroaryldihydropyrimidine Based Hepatitis B Virus (HBV) Capsid Inhibitors", Journal of Medicinal Chemistry, vol. 59: pp. 7651-7666, (2016).
Shi, et al, "NMR-spectroscopy-based metanonomic approach to the analysis of Bay41-4109, a novel anti-HBV compound, induced hepatotoxcity in rats", Toxicology Letters, vol. 173: pp. 161-167 (2007).
Stalder, et al, "Selective antagonists of mouse trace amine-associated receptor 1 (mTAAR1): Discovery of EPPTB (R05212773)", Bioorganic & Medicinal Chemistry Letters, vol. 21: pp. 1227-1231 (Dec. 21, 2010).
Stray, et al, "A Heteroaryldihydropyrimidine Activates and Can Misdirect Hepatitis B Virus Capsid Assembly", PNAS, vol. 102(23): pp. 8138-8143 (Jun. 7, 2005).
Stray, et al, "Bay 41-4109 has multiple effects on Hepatitis B virus capsid assembly", Journal of Molecular Recognition, vol. 19: pp. 542-548 (2006).
Tan, et al., Genetically Altering the Thermodynamics and Kinetics of Hepatitis B Virus Capsid Assembly has Profound Effects on Virus Replication in Cell Culture, Journal of Virology, vol. 87(6): pp. 3208-3216 (Mar. 2013).
The Merk Index "Infliximab", An Encyclopedia of Chemicals, Drugs and Biologicals, 14th Ed., p. 924 (2013).
The Merk Index, "Zidovudine", An Encyclopedia of Chemicals, Drugs and Biologicals, 14th Ed., p. 1885 (2013).
Wang, et al., "In vitro inhibition of HBV replication by a novel compound, GLS4, and its efficacy against adefovir-dipovoxil-resistant HBV mutations", Antiviral Therapy, vol. 17:pp. 793-803 (2012).
Wang, et al., "Serum hepatitis B virus RNS is encapsidated pregenome RNA that may be associated with persistence of viral infection and rebound", Journal of Hepatology, vol. 65: pp. 700-710(2016).
Wang, et al, "Synthesis and Evaluation of Benzothiazole-Based Analogues as Novel, Potent, and Selective Fatty Acid Amide Hydrolase Inhibitors", J. Med. Chem., vol. 52: pp. 170-180 (2009).
Watanabe, et al, "Ortho lithiation of N,N-dimethylbenzenesulfunamide by n-butyllithium. Condensation with electrophilic compounds", Candian Journal of Chemistry, vol. 47: pp. 1543-1546 (Oct. 30, 1968).
Weber, et al, "Inhibition of human hepatitis B virus (HBV) by a novel non-nucleosidic compound in a transgenic mouse model", Antiviral Research, vol. 54 (2): pp. 69-78 (Jan. 1, 2002).
West, "Chapter 10 Solid Solutions", Solid State Chemistry and Its Applications, John Wiley & Sons, pp. 33-36 (1984).
Wu, et al., "Preclinical Characterization of GLS4, an Inhibitor of Hepatitis B Virus Core Particle Assembly", Antimicrobial Agents and Chemotherapy, vol. 57(11): pp. 5344-5354 (Nov. 2013).
Yang, et al., "Effects of a Hepatitis B Virus Inhibitor, NZ-4, on Capsid Formation", Antiviral Research, vol. 125: pp. 25-33 (2016).
Yang, et al., "Isothiafludine, a novel non-nucleoside compound inhibits hepatitis B virus replication through blocking pregenomic RNA encapsidation", Acta Pharmacologica Sinica, vol. 35: pp. 410-418 (2014).
Yogaratnam, et al., "Safety, Tolerability and Pharmacokentics of JNJ 56136379, a Novel HBV Capsid Assembly Modulator in Healthy Subjects", The Abstracts of the Liver Meeting 2016 (AASLD), Abstract 1881: pp. 930A-931A, Boston, MA (Oct. 2016).
Yuen, et al, "ARC-520 Produces Deep and Durable Knockdown of Viral Antigen and DNA in Phase II Study in Patients with Chronic Hepatitis B", The Abstracts of the Liver Meeting 2015, Abstract LB-10, pp. 1385A-1386A, San Francisco, CA (Oct. 2015).
Yuen, et al, "NVR 3-778, a first-in-class HBV core inhibitor, alone and in combination with PEG-Interferon (PEGIFN), in treatment-naive HBEAG-positive patients: early reductions in HBV DNA and HBEAG", The Abstracts of the International Liver Congress (EASL), Abstract LB-06: pp. S210-S211 (Oct. 2016).
Zlotnick, et al., "Core Protein: A pleiotropic Keystone in the HBV Lifecycle", Antiviral Research, vol. 121: pp. 82-93 (2015).
Zoulim, et al., "Current Treatments for Chronic Hepatitis B Virus Infections", Current Opinion in Virology, vol. 18: pp. 109-116 (2016).
Carver, et al., Polyfunctionalisation of Imidazole via Sequential Imidazolyl Anion Formation, Tetrahedron, 1997, pp. 14481-14496, vol. 53 Issue 42.
Gang Liu et al, discovery of Highly Potent and Selective Pan-Aurora Kinase Inhibitors with Enhanced in Vivo Antitumor Therapeutic Index, Journal of Medicinal chemistry, Mar. 1, 2012, pp. 3250-3260, vol. 55.
Online Registry Via STN, Aug. 13, 2012, RN 1390589-54-4.
Online Registry Via STN Feb. 2, 2007, RN 919040-39-4.
Online Registry Via STN Feb. 2, 2007, RN 919040-53-2.
Online Registry Via STN Feb. 2, 2007, RN 919040-55-4.
Online Registry Via STN Dec. 8, 2012, RN 1389720-57-3.
Online Registry Via STN Dec. 11, 2007, RN 957487-45-5.
Online Registry Via STN Dec. 11, 2007, RN 957487-49-9.
Online Registry Via STN Aug. 12, 2012, RN 1389686-79-6.
Online Registry Via STN Mar. 17, 2013, RN 1424462-66-7.
Online Registry Via STN Sep. 18, 2012, RN 1394742-82-5.
Online Registry Via STN, Feb. 2, 2007, RN 919040-37-2.
Online Registry Via STN, Sep. 6, 2011, RN 1328738-57-3.
Online Registry Via STN, Apr. 28, 2011, RN 1286906-97-5.
Online Registry Via STN. Apr. 19, 2008, RN 930914-71-9.
You et al, Pharmaceutical Chemistry, Chemical Industry Press, Jan. 31, 2014, pp. 32-33.

* cited by examiner

SULPHAMOYLTHIOPHENAMIDE DERIVATIVES AND THE USE THEREOF AS MEDICAMENTS FOR THE TREATMENT OF HEPATITIS B

CROSS-REFERENCE TO RELATED APPLICATIONS

This application is the national stage filing under USC 371 of international application PCT/EP2014/060132 filed on May 16, 2014, which claims priority to European Patent Application No. 13168295.7 filed 17 May 2013, European Patent Application No. 13185227.9 filed 19 Sep. 2013, and European Patent Application No. 14157917.7 filed 5 Mar. 2014, the complete disclosures of which are hereby incorporated herein by reference for all purposes.

BACKGROUND ART

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

HBV has caused epidemics in parts of Asia and Africa, and it is endemic in China. HBV has infected approximately 2 billion people worldwide of which approximately 350 million people have developed chronic infections. The virus causes the disease hepatitis B and chronic infection is correlated with a strongly increased risk for the development cirrhosis and hepatocellular carcinoma.

Transmission of hepatitis B virus results from exposure to infectious blood or body fluids, while viral DNA has been detected in the saliva, tears, and urine of chronic carriers with high titer DNA in serum.

An effective and well-tolerated vaccine exists, but direct treatment options are currently limited to interferon and the following antivirals; tenofovir, lamivudine, adefovir, entecavir and telbivudine.

In addition, heteroaryldihydropyrimidines (HAPs) were identified as a class of HBV inhibitors in tissue culture and animal models (Weber et al., Antiviral Res. 54: 69-78).

WO2013/006394, published on Jan. 10, 2013 relates to a subclass of Sulphamoyl-arylamides active against HBV.

WO2013/096744, published on June 26, also relates to relates to a subclass of Sulphamoyl-arylamides active against HBV.

In addition, WO2014/033170 and WO2014/033176, published on Mar. 6, 2014 relate further compounds active against HBV.

Amongst the problems which HBV direct antivirals may encounter are toxicity, mutagenicity, lack of selectivity, poor efficacy, poor bioavailability, and difficulty of synthesis.

There is a need for additional HBV inhibitors that may overcome at least one of these disadvantages or that have additional advantages such as increased potency or an increased safety window.

DESCRIPTION OF THE INVENTION

The present invention relates to a compound of Formula (I)

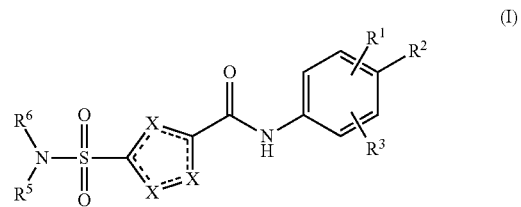

or a stereoisomer or tautomeric form thereof, wherein:
One X is S and the other two X represent $CR^4$;
$R^2$ is Fluoro or Hydrogen;
$R^1$ and $R^3$ are independently selected from the group consisting of Hydrogen, Fluoro, Chloro, Bromo, $CHF_2$, $CH_2F$, $CF_3$, —CN and methyl, wherein at least one of $R^1$ and $R^3$ is not Hydrogen and $R^1$ and $R^3$ are not ortho methyl or ortho Chloro;
One $R^4$ is Hydrogen, and the other $R^4$ is selected from the group consisting of Hydrogen, halogen, $C_1$-$C_3$alkyl, cyclopropyl, $CHF_2$, $CH_2F$ and $CF_3$;
$R^5$ is Hydrogen;
$R^6$ is selected from the group consisting of $C_1$-$C_6$alkyl, $C_1$-$C_3$alkyl-$R^7$ and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, Fluoro, OH, $CF_3$ and $C_1$-$C_4$alkyl;
$R^7$ is a 3-7 membered saturated ring optionally containing one or more heteroatoms each independently selected from the group consisting of O, S and N, or C(=O)—$R^8$;
$R^8$ is selected from the group consisting of $C_1$-$C_3$alkoxy and —$NH_2$;
wherein if $R^1$ is Methyl, $R^2$ is Fluoro, and $R^3$ is Hydrogen, $R^6$ is not Methyl;
or a pharmaceutically acceptable salt or a solvate thereof.

The invention further relates to a pharmaceutical composition comprising a compound of Formula (I), and a pharmaceutically acceptable carrier.

The invention also relates to the compounds of formula (I) for use as a medicament, preferably for use in the prevention or treatment of an HBV infection in a mammal.

In a further aspect, the invention relates to a combination of a compound of formula (I), and another HBV inhibitor.

DEFINITIONS

The term "$C_{1-3}$alkyl" as a group or part of a group refers to a hydrocarbyl radical of Formula $C_nH_{2n+1}$ wherein n is a number ranging from 1 to 3. In case $C_{1-3}$alkyl is coupled to a further radical, it refers to a Formula $C_nH_{2n}$. $C_{1-3}$alkyl groups comprise from 1 to 3 carbon atoms, more preferably 1 to 2 carbon atoms. $C_{1-3}$alkyl includes all linear, or branched alkyl groups with between 1 and 3 carbon atoms, and thus includes such as for example methyl, ethyl, n-propyl, and i-propyl.

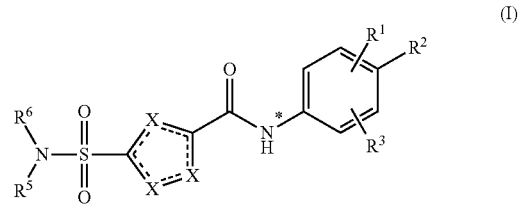

(I)

$C_{1-4}$alkyl as a group or part of a group defines straight or branched chain saturated hydrocarbon radicals having from 1 to 4 carbon atoms such as the group defined for $C_{1-3}$alkyl and butyl and the like.

$C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like.

The term "$C_{1-3}$alkyloxy" as a group or part of a group refers to a radical having the Formula —OR$^c$ wherein R$^c$ is $C_{1-3}$alkyl. Non-limiting examples of suitable $C_{1-3}$alkyloxy include methyloxy (also methoxy), ethyloxy (also ethoxy), propyloxy and isopropyloxy.

As used herein, the term "3-7 membered saturated ring" means saturated cyclic hydrocarbon with 3, 4, 5, 6 or 7 carbon atoms and is generic to cyclopropyl, cyclobutyl, cyclopentyl, cyclohexyl and cycloheptyl.

Such saturated ring optionally contains one or more heteroatoms, such that at least one carbon atom is replaced by a heteroatom selected from N, O and S, in particular from N and O. Examples include oxetane, tetrahydro-2H-pyranyl, piperidinyl, tetrahydrofuranyl, morpholinyl, thiolane 1,1-dioxide and pyrrolidinyl. Preferred are saturated cyclic hydrocarbon with 3 or 4 carbon atoms and 1 oxygen atom. Examples include oxetane, and tetrahydrofuranyl.

It should be noted that different isomers of the various heterocycles may exist within the definitions as used throughout the specification. For example, pyrrolyl may be 1H-pyrrolyl or 2H-pyrrolyl.

The term halo and halogen are generic to Fluoro, Chloro, Bromo or Iodo. Preferred halogens are Fluoro and Chloro.

It should also be noted that the radical positions on any molecular moiety used in the definitions may be anywhere on such moiety as long as it is chemically stable. For instance pyridyl includes 2-pyridyl, 3-pyridyl and 4-pyridyl; pentyl includes 1-pentyl, 2-pentyl and 3-pentyl.

The following graphical representation ----- indicates a single or double bond in an aromatic or partially aromatic structure, as far as chemically feasible. As used herein,

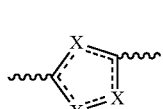

thus represents

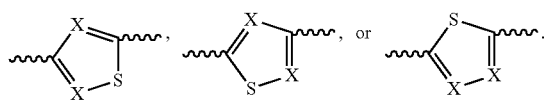

Positions indicated on phenyl (e.g. ortho, meta and/or para) are indicated relative to the bond connecting the phenyl to the main structure. An example with regard to the position of R$^1$, any location is indicated relative to the nitrogen (*) connected to the main structure:

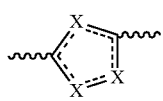

When any variable (e.g. halogen or $C_{1-4}$alkyl) occurs more than one time in any constituent, each definition is independent.

For therapeutic use, the salts of the compounds of formula (I) are those wherein the counter ion is pharmaceutically or physiologically acceptable. However, salts having a pharmaceutically unacceptable counter ion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; hemisulphuric, nitric; phosphoric and the like acids; or organic acids such as, for example, acetic, aspartic, dodecylsulphuric, heptanoic, hexanoic, nicotinic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The term "salts" also comprises the hydrates and the solvent addition forms that the compounds of the present invention are able to form. Examples of such forms are e.g. hydrates, alcoholates and the like.

The present compounds may also exist in their tautomeric forms For example, tautomeric forms of amide (—C(=O)—NH—) groups are iminoalcohols (—C(OH)=N—). Tautomeric forms, although not explicitly indicated in the structural formulae represented herein, are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric forms of formula (I) can be obtained separately by conventional methods. Appropriate physical separation methods that may advantageously be employed are, for example, selective crystallization and chromatography, e.g. column chromatography.

The present invention is also intended to include all isotopes of atoms occurring on the present compounds. Isotopes include those atoms having the same atomic number but different mass numbers. By way of general example and without limitation, isotopes of Hydrogen include tritium and deuterium. Isotopes of carbon include C-13 and C-14.

DETAILED DESCRIPTION OF THE INVENTION

Whenever used hereinafter, the term "compounds of formula (I)",

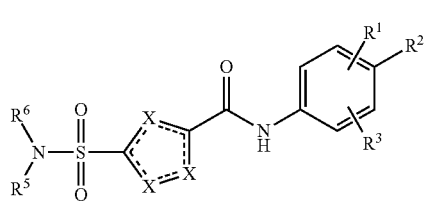

or "the present compounds" or similar term is meant to include the compounds of general formula (I), (IA), (II), salts, stereoisomeric forms and racemic mixtures or any subgroups thereof.

In a first aspect, the invention provides compound of Formula (I)

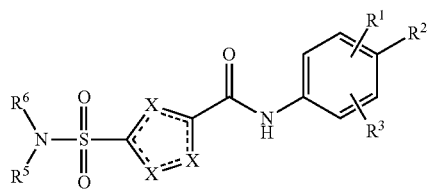

or a stereoisomer or tautomeric form thereof, wherein:
One X is S and the other two X represent $CR^4$;
$R^2$ is Fluoro or Hydrogen;
$R^1$ and $R^3$ are independently selected from the group consisting of Hydrogen, Fluoro, Chloro, Bromo, $CHF_2$, $CH_2F$, $CF_3$, —CN and methyl, wherein at least one of $R^1$ and $R^3$ is not Hydrogen and $R^1$ and $R^3$ are not ortho methyl or ortho Chloro;
One $R^4$ is Hydrogen, and the other $R^4$ is selected from the group consisting of Hydrogen, halogen, $C_1$-$C_3$alkyl, cyclopropyl, $CHF_2$, $CH_2F$ and $CF_3$;
$R^5$ is Hydrogen;
$R^6$ is selected from the group consisting of $C_1$-$C_6$alkyl, $C_1$-$C_3$alkyl-$R^7$ and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, Fluoro, OH, $CF_3$ and $C_1$-$C_4$alkyl;
$R^7$ is a 3-7 membered saturated ring optionally containing one or more heteroatoms each independently selected from the group consisting of O, S and N, or C(=O)—$R^8$;
$R^8$ is selected from the group consisting of $C_1$-$C_3$alkoxy and —$NH_2$;
or a pharmaceutically acceptable salt or a solvate thereof.
In one embodiment, if $R^1$ is Methyl, $R^2$ is Fluoro, and $R^3$— Hydrogen, $R^6$ is not Methyl;
In another embodiment, the invention provides compound of Formula (I) wherein:
One X is S and the other two X represent $CR^4$;
$R^2$ is Fluoro or Hydrogen;
$R^1$ and $R^3$ are independently selected from the group consisting of Hydrogen, Fluoro, Chloro, Bromo, $CHF_2$, $CH_2F$, $CF_3$ and methyl, wherein at least one of $R^1$ and $R^3$ is not Hydrogen;
One $R^4$ is Hydrogen, and the other $R^4$ is selected from the group consisting of Hydrogen, halogen, $C_1$-$C_3$alkyl, cyclopropyl, $CHF_2$, $CH_2F$ and $CF_3$;
$R^5$ is Hydrogen;
$R^6$ is selected from the group consisting of $C_1$-$C_6$alkyl, $C_1$-$C_3$alkyl-$R^7$ and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, Fluoro, OH and $C_1$-$C_4$alkyl;
$R^7$ is a 3-7 membered saturated ring optionally containing one or more heteroatoms each independently selected from the group consisting of O, S and N;
wherein if $R^1$ is Methyl, $R^2$ is Fluoro, and $R^3$— Hydrogen, $R^6$ is not Methyl;

or a pharmaceutically acceptable salt or a solvate thereof.

Furthermore, the invention provides compounds of Formula (I) or a stereoisomer or tautomeric form thereof, wherein:

One X is S and the other two X represent $CR^4$;

$R^2$ is Fluoro or Hydrogen;

$R^1$ and $R^3$ are independently selected from the group consisting of Hydrogen, Fluoro, Chloro, Bromo, $CHF_2$, $CH_2F$, $CF_3$ and methyl, wherein at least one of $R^1$ and $R^3$ is not Hydrogen;

One $R^4$ is Hydrogen, and the other $R^4$ is selected from the group consisting of Hydrogen, halogen, $C_1$-$C_3$alkyl, cyclopropyl, $CHF_2$, $CH_2F$ and $CF_3$;

$R^5$ is Hydrogen;

$R^6$ is selected from the group consisting of $C_1$-$C_6$alkyl and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, OH and $C_1$-$C_4$alkyl;

wherein if $R^1$ is Methyl, $R^2$ is Fluoro, and $R^{3-}$ Hydrogen, $R^6$ is not Methyl.

or a pharmaceutically acceptable salt or a solvate thereof.

In another aspect compounds according to Formula (II) are provided:

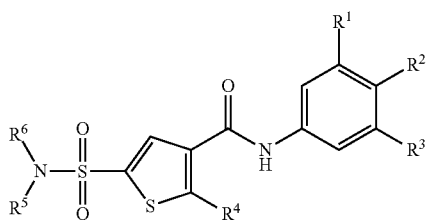

(II)

wherein $R^4$ is selected from the group consisting of Hydrogen, halogen, $C_1$-$C_3$alkyl, cyclopropyl, $CHF_2$, $CH_2F$ and $CF_3$ and the other substituents are as defined in this specification.

In another embodiment compounds according to Formula (I) (II) or (II), or a stereoisomer or tautomeric form thereof are provided (I)

(IA)

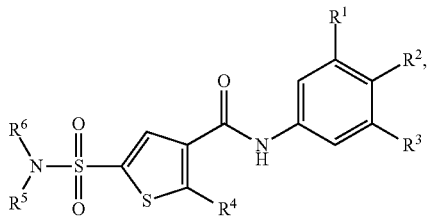

(II)

wherein:

One X is S and the other two X represent $CR^4$;

$R^2$ is Fluoro or Hydrogen;

$R^1$ and $R^3$ are independently selected from the group consisting of Hydrogen, Fluoro, Chloro, Bromo, $CHF_2$, $CH_2F$, $CF_3$, —CN and methyl;

One $R^4$ is Hydrogen, and the other $R^4$ is selected from the group consisting of Hydrogen, halogen, $C_1$-$C_3$alkyl, cyclopropyl, $CHF_2$, $CH_2F$ and $CF_3$;

$R^5$ is Hydrogen;

$R^6$ is selected from the group consisting of $C_1$-$C_6$alkyl, $C_1$-$C_3$alkyl-$R^7$ and a 3-7 membered saturated ring optionally containing one or more heteroatoms each independently selected from the group consisting of O, S and N, such 3-7 membered saturated ring or $C_1$-$C_6$alkyl optionally being substituted with one or more substituents each independently selected from the group consisting of Hydrogen, Fluoro, OH, $CF_3$ and $C_1$-$C_4$alkyl;

$R^7$ is a 3-7 membered saturated ring optionally containing one or more heteroatoms each independently selected from the group consisting of O, S and N, or C(=O)—$R^8$;

$R^8$ is selected from the group consisting of $C_1$-$C_3$alkoxy and —$NH_2$;

or a pharmaceutically acceptable salt or a solvate thereof.

Another embodiment of the present invention relates to those compounds of formula (I) or any subgroup thereof as mentioned in any of the other embodiments wherein one or more of the following restriction applies:

a) $R^1$ is selected from either Fluoro or methyl.

b) at least 2 of $R^1$ and $R^2$ and $R^3$ are Halogen. In a further embodiment, $R^1$ is methyl and $R^2$ is Fluoro.

c) $R^6$ is a branched $C_1$-$C_6$alkyl optionally substituted with one or more Fluoro.

d) $R^6$ contains a 3-7 membered saturated ring optionally containing one oxygen, preferably $R^6$ is a 4 or 5 membered saturated ring containing one oxygen.

Further combinations of any of the sub- or preferred embodiments are also envisioned to be in the scope of the present invention.

Preferred compounds according to the invention are compounds or a stereoisomer or tautomeric form thereof with a formula selected from table 1.

In a further aspect, the present invention concerns a pharmaceutical composition comprising a therapeutically or prophylactically effective amount of a compound of formula (I) as specified herein, and a pharmaceutically acceptable carrier. A prophylactically effective amount in this context is an amount sufficient to prevent HBV infection in subjects being at risk of being infected. A therapeutically effective amount in this context is an amount sufficient to stabilize HBV infection, to reduce HBV infection, or to eradicate HBV infection, in infected subjects. In still a further aspect, this invention relates to a process of preparing a pharmaceutical composition as specified herein, which comprises intimately mixing a pharmaceutically acceptable carrier with a therapeutically or prophylactically effective amount of a compound of formula (I), as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. The compounds of the present invention may also be administered via oral inhalation or insufflation in the form of a solution, a suspension or a dry powder using any art-known delivery system.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) are active as inhibitors of the HBV replication cycle and can be used in the treatment and prophylaxis of HBV infection or diseases associated with HBV. The latter include progressive liver fibrosis, inflammation and necrosis leading to cirrhosis, end-stage liver disease, and hepatocellular carcinoma.

Due to their antiviral properties, particularly their anti-HBV properties, the compounds of formula (I) or any subgroup thereof, are useful in the inhibition of the HBV replication cycle, in particular in the treatment of warm-blooded animals, in particular humans, infected with HBV, and for the prophylaxis of HBV infections. The present invention furthermore relates to a method of treating a warm-blooded animal, in particular human, infected by HBV, or being at risk of infection by HBV, said method comprising the administration of a therapeutically effective amount of a compound of formula (I).

The compounds of formula (I), as specified herein, may therefore be used as a medicine, in particular as medicine to treat or prevent HBV infection. Said use as a medicine or method of treatment comprises the systemic administration to HBV infected subjects or to subjects susceptible to HBV infection of an amount effective to combat the conditions associated with HBV infection or an amount effective to prevent HBV infection.

The present invention also relates to the use of the present compounds in the manufacture of a medicament for the treatment or the prevention of HBV infection.

In general it is contemplated that an antiviral effective daily amount would be from about 0.01 to about 50 mg/kg, or about 0.01 to about 30 mg/kg body weight. It may be appropriate to administer the required dose as two, three, four or more sub-doses at appropriate intervals throughout the day. Said sub-doses may be formulated as unit dosage forms, for example, containing about 1 to about 500 mg, or about 1 to about 300 mg, or about 1 to about 100 mg, or about 2 to about 50 mg of active ingredient per unit dosage form.

The present invention also concerns combinations of a compound of formula (I) or any subgroup thereof, as specified herein with other anti-HBV agents. The term "combination" may relate to a product or kit containing (a) a compound of formula (I), as specified above, and (b) at least one other compound capable of treating HBV infection (herein designated as anti-HBV agent), as a combined preparation for simultaneous, separate or sequential use in treatment of HBV infections. In an embodiment, the invention concerns combination of a compound of formula (I) or any subgroup thereof with at least one anti-HBV agent. In a particular embodiment, the invention concerns combination of a compound of formula (I) or any subgroup thereof with at least two anti-HBV agents. In a particular embodiment, the invention concerns combination of a compound of formula (I) or any subgroup thereof with at least three anti-HBV agents. In a particular embodiment, the invention concerns combination of a compound of formula (I) or any subgroup thereof with at least four anti-HBV agents.

The combination of previously known anti-HBV agents, such as interferon-$\alpha$ (IFN-$\alpha$), pegylated interferon-$\alpha$, 3TC, adefovir or a combination thereof, and, a compound of formula (I) or any subgroup thereof can be used as a medicine in a combination therapy.

Generic Synthesis:

The substituents in this general synthesis section are meant to include any substituent or reactive species that is suitable for transformation into any substituent according to the present invention without undue burden for the person skilled in the art.

A possible synthesis of compound of general formula (I) is described in scheme 1 and 2. A carboxylic acid chloride of general formula (III) (for example synthesized according to chemical process of compound 1 or 2 or as described for the synthesis of 5-chlorosulfonyl-2-methyl-thiophene-3-carbonyl chloride) can be selectively reacted with an aniline of general formula (IV), for example by slow addition of aniline IV to a refluxing solution of compound III in toluene, resulting in compound V. The remaining sulfonic acid chloride functionality in compound V is further reacted with an amine of general formula (VI), resulting in a compound of general formula (I).

Scheme 1

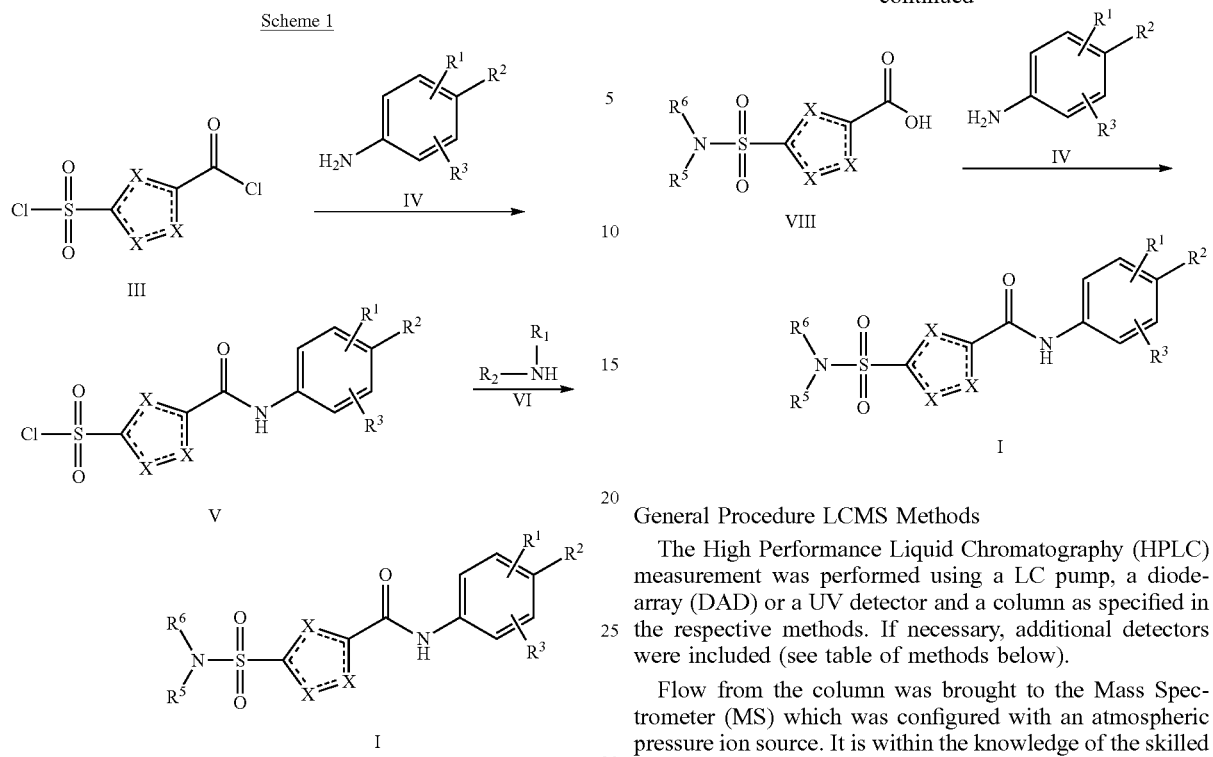

Alternatively a compound of general formula (I) might be obtained as described in scheme 2. This time the sulfonic acid chloride VII (for example synthesized according to chemical process of compound 2 or as described for 5-chlorosulfonyl-2-methyl-thiophene-3-carboxylic acid) is reacted with an amine of general formula (VI), for example in an organic solvent like $CH_2Cl_2$ in the presence of an organic base like triethylamine or DIPEA. The formed compound VIII is coupled with aniline of general formula (IV) in the presence of an activating reagent like for example HATU and an organic base like triethylamine or DIPEA.

Scheme 2

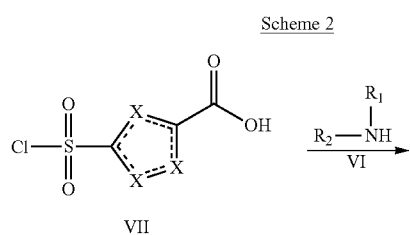

General Procedure LCMS Methods

The High Performance Liquid Chromatography (HPLC) measurement was performed using a LC pump, a diode-array (DAD) or a UV detector and a column as specified in the respective methods. If necessary, additional detectors were included (see table of methods below).

Flow from the column was brought to the Mass Spectrometer (MS) which was configured with an atmospheric pressure ion source. It is within the knowledge of the skilled person to set the tune parameters (e.g. scanning range, dwell time . . . ) in order to obtain ions allowing the identification of the compound's nominal monoisotopic molecular weight (MW). Data acquisition was performed with appropriate software.

Compounds are described by their experimental retention times ($R_t$) and ions. If not specified differently in the table of data, the reported molecular ion corresponds to the [M+H]$^+$ (protonated molecule) and/or [M−H]$^-$ (deprotonated molecule). In case the compound was not directly ionizable the type of adduct is specified (i.e. [M+NH$_4$]$^+$, [M+HCOO]$^-$, etc. . . . ). All results were obtained with experimental uncertainties that are commonly associated with the method used.

Hereinafter, "SQD" means Single Quadrupole Detector, "MSD" Mass Selective Detector, "RT" room temperature, "BEH" bridged ethylsiloxane/silica hybrid, "DAD" Diode Array Detector, "HSS" High Strength silica., "Q-Tof" Quadrupole Time-of-flight mass spectrometers, "CLND", ChemiLuminescent Nitrogen Detector, "ELSD" Evaporative Light Scanning Detector, LCMS Methods (Flow expressed in mL/min; column temperature (T) in ° C.; Run time in minutes).

| Method | Instrument | Column | Mobile phase | Gradient | Flow Col T | Run time |
|---|---|---|---|---|---|---|
| A | Waters: Acquity ® UPLC ®-DAD and SQD | Waters: HSS T3 (1.8 µm, 2.1*100 mm) | A: 10 mM CH$_3$COONH$_4$ in 95% H$_2$O + 5% CH$_3$CN B: CH$_3$CN | From 100% A to 5% A in 2.10 min, to 0% A in 0.90 min, to 5% A in 0.5 min | 0.8 55 | 3.5 |
| B | Waters : Acquity ® UPLC ®-DAD and SQD | Waters: BEH C18 (1.7 µm, 2.1*50 mm) | A: 10 mM CH$_3$COONH$_4$ in 95% H$_2$O + 5% CH$_3$CN B: CH$_3$CN | From 95% A to 5% A in 1.3 min, held for 0.7 min. | 0.8 55 | 2 |

| Method | Instrument | Column | Mobile phase | Gradient | Flow Col T | Run time |
|---|---|---|---|---|---|---|
| C | Agilent: 1100/1200- DAD and MSD | Agilent: TC-C18 (5 µm, 2.1 × 50 mm) | A: CF$_3$COOH 0.1% in water, B: CF$_3$COOH 0.05% in CH$_3$CN | 100% A for 1 min, to 40% A in 4 min, to 15% A in 2.5 min, back to 100% A in 2 min. | 0.8 50 | 10.5 |
| D | Agilent: 1100/1200- DAD and MSD | Agilent: TC-C18 (5 µm, 2.1 × 50 mm) | A: CF$_3$COOH 0.1% in water, B: CF$_3$COOH 0.05% in CH$_3$CN | 90% A for 0.8 min, to 20% A in 3.7 min, held for 3 min, back to 90% A in 2 min. | 0.8 | 10.5 |
| E | Agilent 1100- UV 220 nm | YMC- PACK ODS-AQ, 50 × 2.0 mm 5 µm | A: 0.1% TFA in H$_2$O B: 0.05 TFA in CH$_3$CN | 100% A held for 1 min from 100% A to 40% A in 4 min, held for 2.5 min, to 100% A in 0.5 min held for 2 min. | 0.8 50 | 10.0 |
| F | Agilent 1100- UV 220 nm | YMC- PACK ODS-AQ, 50 × 2.0 mm 5 µm | A: 0.1% TFA in H2O B: 0.05 TFA in CH3CN | 90% A held for 0.8 min From 90% A to 20% A in 3.7 min, held for 3 min, to 90% A in 0.5 min held for 2 min. | 0.8 50 | 10.0 |
| G | Agilent: 1100/1200- DAD and MSD | Waters: xBridge™ Shield RP18 (5 µm, 2.1 × 50 mm) | A: NH$_4$OH 0.05% in water, B: CH$_3$CN | 100% A for 1 min, to 40% A in 4 min, held for 2.5 min, back to 100% A in 2 min. | 0.8 40 | 10.5 |
| H | Agilent: 1100/1200- DAD and MSD | Agilent: TC-C18 (5 µm, 2.1 × 50 mm) | A: CF$_3$COOH 0.1% in water, B: CF$_3$COOH 0.05% in CH$_3$CN | 1 min, to 40% A in 4 min, to 15% A in 2.5 min, back to 100% A in 2 min. | 50 | |

Compound 1: N-(4-fluoro-3-methyl-phenyl)-5-[[(3S)-tetrahydrofuran-3-yl]sulfamoyl]thiophene-3-carboxamide

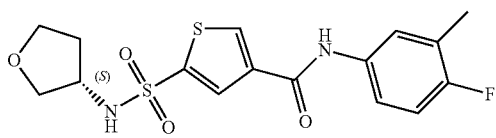

A solution of oxalyl chloride (4670 mg, 36.8 mmol) in dichloromethane (20 mL) was added to 5-(chlorosulfonyl)-3-thiophenecarboxylic acid (1668 mg, 7.36 mmol) and DMF (0.05 equiv) in dichloromethane (50 mL) and stirred overnight. The reaction mixture was concentrated yielding 5-chlorosulfonylthiophene-3-carbonyl chloride as a yellow resin (1845 mg) which was used as such in the next step. $^1$H NMR (400 MHz, CHLOROFORM-d) δ ppm 8.29 (d, J=1.0 Hz, 1H), 8.69 (d, J=1.0 Hz, 1H). 4-fluoro-3-methylaniline (939 mg, 7.51 mmol) dissolved in toluene (10 mL) was added dropwise to a solution of 5-chlorosulfonylthiophene-3-carbonyl chloride (1.84 g, 7.51 mmol) in toluene (50 mL) at reflux over 5 minutes. The reaction mixture was refluxed 45 minutes and next allowed to reach room temperature. A solution of (S)-(-)-3-amino-tetrahydrofuran p-toluenesulfonate (2141 mg, 8.26 mmol) and DIPEA (3.75 mL, 21.8 mmol) in CH$_2$Cl$_2$ (25 mL) was added and the reaction mixture was stirred overnight. The mixture was washed with 1M HCl (100 mL). A light purple precipitate was filtered off. The layers were separated and the water layer was extracted with dichloromethane (150 mL). The organic layers were washed with 1M HCl (2x), water, NaHCO$_3$ (150 mL) solution, dried over sodium sulphate, filtered and concentrated. The obtained residue was purified by silica gel column chromatography using a gradient from 5 to 10% CH$_3$OH in dichloromethane. The obtained residue was repurified using a gradient from 25 to 100% EtOAc. The product fractions were concentrated and dried yielding compound 1 as a white powder (1431 mg). Method A; Rt: 1.52 min. m/z: 385.0 (M+H)$^+$ Exact mass: 384.1. $^1$H NMR (400 MHz, DMSO-d$_6$) δ ppm 1.65-1.73 (m, 1H), 1.95-2.04 (m, 1H), 2.24 (d, J=1.6 Hz, 3H), 3.44 (dd, J=8.9, 4.4 Hz, 1H), 3.62 (td, J=8.1, 5.8 Hz, 1H), 3.67-3.77 (m, 2H), 3.80-3.88 (m, 1H), 7.13 (t, J=9.3 Hz, 1H), 7.56 (ddd, J=8.8, 4.5, 2.8 Hz, 1H), 7.64 (dd, J=7.3, 2.4 Hz, 1H), 8.14 (d, J=1.6 Hz, 1H), 8.30 (d, J=4.8 Hz, 1H), 8.62 (d, J=1.6 Hz, 1H), 10.22 (s, 1H).

Compound 2: 2-bromo-N-(4-fluoro-3-methyl-phenyl)-5-[[(3S)-tetrahydrofuran-3-yl]-sulfamoyl]thiophene-3-carboxamide

Synthesis of 2-bromo-5-chlorosulfonyl-thiophene-3-carboxylic acid 2-bromo-3-thiophenecarboxylic acid (5000 mg, 24.15 mmol) was dissolved portion wise in chlorosulfonic acid (8 mL) in a microwave tube and heated at 95° C. for 2 hours. The reaction mixture was carefully added dropwise to a, ice/water (300 mL) mixture and stirred for 5 minutes. The formed precipitate was filtered off, rinsed with water and dried in vacuo at 50° C., yielding 2-bromo-5-chlorosulfonyl-thiophene-3-carboxylic acid as a beige powder (5856 mg).) Compound 2 was synthesized similar as described for compound 1, starting from 2-bromo-5-chlorosulfonyl-thiophene-3-carboxylic acid instead of 5-(chlorosulfonyl)-3-thiophenecarboxylic acid. After work up, the compound was purified by silica gel column chromatography by gradient elution with 10 to 100% EtOAc in heptanes. The obtained solid was recrystallized by adding water to a warm solution of crude compound 2 (11.4 g) in methanol (200 mL). After filtration and drying in vacuo at 50° C., compound 2 was obtained as a beige powder (9850 mg). Method B; Rt: 0.98 min. m/z: 482.0 (M+NH$_4$)$^+$ Exact mass: 464.0. $^1$H NMR (400 MHz, DMSO-d$_6$) δ ppm 1.65-1.78 (m, 1H), 1.96-2.10 (m, 1H), 2.24 (d, J=1.8 Hz, 3H), 3.46 (dd, J=9.0, 4.2 Hz, 1H), 3.63 (td, J=8.1, 5.7 Hz, 1H), 3.69-3.78 (m, 2H), 3.81-3.91 (m, 1H), 7.13 (t, J=9.2 Hz, 1H), 7.51 (dt, J=7.6, 4.0 Hz, 1H), 7.62 (dd, J=6.8, 2.2 Hz, 1H), 7.87 (s, 1H), 8.42 (d, J=6.2 Hz, 1H), 10.38 (s, 1H).

Compound 3: 2-chloro-N-(4-fluoro-3-methyl-phenyl)-5-[[(1R)-2-hydroxy-1-methyl-ethyl]sulfamoyl]thiophene-3-carboxamide

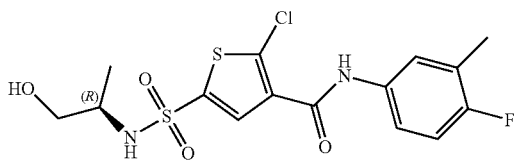

Synthesis of 5-chloro-4-[(4-fluoro-3-methyl-phenyl)carbamoyl]thiophene-2-sulfonyl chloride 4-fluoro-3-methylaniline (2460 mg, 19.6 mmol) dissolved in toluene (5 mL) was added drop wise to a solution of 2-chloro-5-chlorosulfonyl-thiophene-3-carbonyl chloride (prepared from 2-chloro-5-chlorosulfonyl-thiophene-3-carboxylic acid similarly as described for the synthesis of 5-chlorosulfonylthiophene-3-carbonyl chloride from 5-(chlorosulfonyl)-3-thiophenecarboxylic acid, 5492 mg, 19.6 mmol) in toluene (25 mL) at reflux during 5 minutes. The reaction mixture was refluxed 30 minutes and allowed to reach room temperature. After stirring at room temperature for 2 hours the formed precipitate was filtered and the solids were dried in vacuo at 55° C., resulting in 5-chloro-4-[(4-fluoro-3-methyl-phenyl)carbamoyl]thiophene-2-sulfonyl chloride (5.94 g) as an off white powder. Method B; Rt: 1.18 min. m/z: 365.9 (M−H)$^−$ Exact mass: 366.9. 5-chloro-4-[(4-fluoro-3-methyl-phenyl)carbamoyl]thiophene-2-sulfonyl chloride (500 mg, 1.36 mmol) was dissolved in CH$_2$Cl$_2$ (5 mL) and D-alaninol (125 mg, 1.63 mmol) and Hunig's base (0.679 mL, 3.94 mmol) were added and the reaction mixture was stirred at room temperature for 30 minutes. The mixture was washed with 1M HCl (15 mL). The organic layer was dried over magnesium sulphate, filtered and concentrated to afford a brown sticky residue which was sonicated in CH$_2$Cl$_2$ (5 mL) and the white solid was filtered and washed with CH$_2$Cl$_2$ (3 mL) and dried in vacuo at 50° C., resulting in compound 3 as a white solid (351 mg). Method B; Rt: 0.91 min. m/z: 424.0 (M+NH$_4$)$^+$ Exact mass: 406.0. $^1$H NMR (400 MHz, DMSO-d$_6$) δ ppm 1.01 (d, J=6.4 Hz, 3H), 2.24 (d, J=1.5 Hz, 3H), 3.12-3.39 (m, 3H), 4.77 (t, J=5.5 Hz, 1H), 7.13 (t, J=9.1 Hz, 1H), 7.46-7.55 (m, 1H), 7.62 (dd, J=6.9, 2.1 Hz, 1H), 7.88 (s, 1H), 8.05 (br. d, J=6.4 Hz, 1H), 10.37 (br. s, 1H).

Compound 4: 2-chloro-N-(4-fluoro-3-methyl-phenyl)-5-[[(3S)-tetrahydrofuran-3-yl]-sulfamoyl]thiophene-3-carboxamide

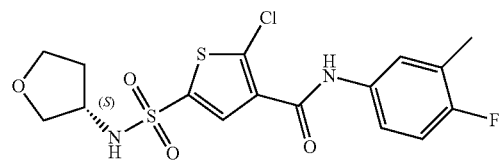

5-chloro-4-[(4-fluoro-3-methyl-phenyl)carbamoyl]thiophene-2-sulfonyl chloride was dissolved in CH$_2$Cl$_2$ (20 mL) and (S)-(−)-3-aminotetrahydrofuran p-toluenesulfonate (1.94 g, 7.47 mmol) and Hunig's Base (3.39 mL, 19.7 mmol) were added and the reaction mixture was stirred at room temperature for 30 minutes. The mixture was washed with HCl (2×40 mL, 1M). Both layers were filtered and the obtained solid was washed with water (10 mL) and CH$_2$Cl$_2$ (10 mL) and dried overnight in vacuo at 50° C. resulting in compound 4 as a white solid (739 mg). The organic layer was dried over magnesium sulphate, filtered and concentrated to afford a brown sticky oil which was sonicated in CH$_2$Cl$_2$ (5 mL) and the resulting white solid was filtered and washed with CH$_2$Cl$_2$ and dried in vacuo at 50° C. resulting in more compound 4 (873 mg) as white solid. The filtrate was evaporated to dryness and the residue was further purified using silica gel column chromatography (ethyl acetate in heptane from 10 to 100%) resulting in more compound 4 (830 mg) as a white powder. Method B; Rt: 0.97 min. m/z: 416.9 (M−H)$^−$ Exact mass: 418.0. $^1$H NMR (400 MHz, DMSO-d$_6$) δ ppm 1.66-1.77 (m, 1H), 1.98-2.10 (m, 1H), 2.24 (d, J=2.0 Hz, 3H), 3.46 (dd, J=9.1, 4.2 Hz, 1H), 3.63 (td, J=8.1, 5.7 Hz, 1H), 3.70-3.76 (m, 2H), 3.81-3.91 (m, 1H), 7.13 (t, J=9.3 Hz, 1H), 7.45-7.55 (m, 1H), 7.61 (dd, J=7.3, 2.4 Hz, 1H), 7.92 (s, 1H), 8.44 (s, 1H), 10.38 (s, 1H). [α]$_D^{20}$: +5° (c 0.44 w/v %, MeOH), DSC: From 30 to 300° C. at 10° C./min, peak: 150° C.

Compound 5: N-(4-fluoro-3-methyl-phenyl)-5-[[(3S)-tetrahydrofuran-3-yl]sulfamoyl]-2-(trifluoromethyl)thiophene-3-carboxamide

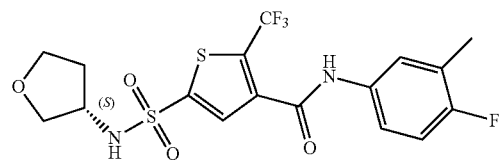

Compound 2 (1000 mg, 2.16 mmol) was dissolved in a mixture of DMF (25 mL) and N-methylmorpholine (1.23 mL, 11.2 mmol) containing Copper(I)Iodide (448 mg, 2.35 mmol) and 2,2-difluoro-2-fluorosulfonyl acetic acid methyl ester (2073 mg, 10.8 mmol). After heating at 70° C., with vigorous stirring, for 2 hours, the mixture was allowed to reach room temperature. Saturated aqueous ammonium chloride solution was added to the reaction mixture. The mixture was stored at room temperature over weekend. The solids were filtered and washed with water (3×50 mL). The solids were purified using silica gel column chromatography (ethyl acetate in heptane from 10 to 100%). The desired fractions were combined and evaporated to keep 50 mL of the solvent. The formed precipitate was filtered and washed with petroleum ether resulting in compound 5 (168 mg) as a white solid after drying in vacuo at 50° C. Method B; Rt: 1.03 min. m/z: 470.1 $(M+NH_4)^+$ Exact mass: 452.1. $^1$H NMR (400 MHz, DMSO-$d_6$) δ ppm 1.68-1.79 (m, 1H), 2.00-2.14 (m, 1H), 2.24 (d, J=1.5 Hz, 3H), 3.48 (dd, J=9.0, 4.2 Hz, 1H), 3.64 (td, J=8.1, 5.9 Hz, 1H), 3.70-3.80 (m, 2H), 3.88-3.97 (m, 1H), 7.14 (t, J=9.1 Hz, 1H), 7.44-7.52 (m, 1H), 7.61 (dd, J=7.0, 2.2 Hz, 1H), 8.09-8.13 (m, 1H), 8.66 (br. s., 1H), 10.60 (br. s, 1H).

Compound 6: 2-cyclopropyl-N-(4-fluoro-3-methyl-phenyl)-5-[[(3S)-tetrahydrofuran-3-yl]sulfamoyl]thiophene-3-carboxamide

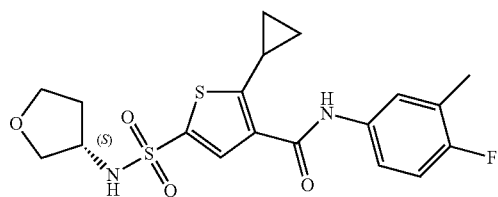

A 10 mL microwave tube was loaded with a stirring bar, potassium cyclopropyl trifluoroborate (191 mg, 1.29 mmol), compound 4 (300 mg, 0.716 mmol), water (388 μL, 21.5 mmol) and 1,2-dimethoxyethane (3.72 mL, 35.8 mmol) and nitrogen gas was bubbled through for 10 minutes. Under a nitrogen atmosphere, cesium carbonate (16.2 mg, 0.0716 mmol), palladium (II) acetate (16.2 mg, 0.0716 mmol) and butyldi-1-adamantylphosphine (41.1 mg, 0.115 mmol) were added together and the reaction mixture was stirred under microwave irradiation at 140° C. for 10 minutes. The reaction mixture was cooled to room temperature. Nitrogen gas was bubbled through the reaction mixture for 10 minutes and Palladium (II) acetate (16.2 mg, 0.0716 mmol) and butyldi-1-adamantylphosphine (41.1 mg, 0.115 mmol) were added together and the reaction mixture was stirred at 140° C. in microwave oven for 40 minutes. The reaction mixture was filtered and the filtrate was diluted with $CH_2Cl_2$ (20 mL). The organic layer was separated and washed with saturated aqueous sodium carbonate solution and water, dried ($Na_2SO_4$) and evaporated to afford a brown residue. The obtained residue was purified using silica gel column chromatography (ethyl acetate in heptane from 10 to 100%) to afford crude compound 6 as off white solid. Crude compound 6 was dissolved in $CH_2Cl_2$ (20 mL) and heptane (50 mL) was added. The solution was evaporated until 50 mL solvent remained. The formed white precipitate was filtered and washed with petroleum ether (2×10 mL) resulting in compound 6 as white powder (174 mg) after drying in vacuo at 50° C. Method B; Rt: 1.00 min. m/z: 442.1 $(M+NH_4)$ Exact mass: 424.1. $^1$H NMR (400 MHz, DMSO-$d_6$) δ ppm 0.73-0.82 (m, 2H), 1.17-1.26 (m, 2H), 1.63-1.74 (m, 1H), 1.94-2.06 (m, 1H), 2.23 (d, J=1.8 Hz, 3H), 2.90-3.00 (m, 1H), 3.42 (dd, J=9.0, 4.4 Hz, 1H), 3.62 (td, J=8.1, 5.9 Hz, 1H), 3.67-3.76 (m, 2H), 3.76-3.84 (m, 1H), 7.11 (t, J=9.1 Hz, 1H), 7.49-7.57 (m, 1H), 7.64 (dd, J=7.0, 2.2 Hz, 1H), 7.90 (s, 1H), 8.18 (br. s., 1H), 10.15 (s, 1H).

Compound 7: N-(4-fluoro-3-methyl-phenyl)-2-methyl-5-[[(3S)-tetrahydrofuran-3-yl]-sulfamoyl]thiophene-3-carboxamide

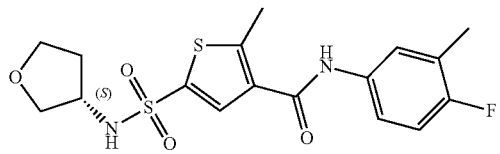

Nitrogen was bubbled through a mixture of compound 2 (830 mg, 1.79 mmol) trimethylboroxine (50% in THF, 5.37 mmol), cesium carbonate (1751 mg, 5.37 mmol) in DME (12 mL) during 5 minutes. 1,1'-bis(diphenylphosphino)ferrocene-palladium(II)dichloride dichloromethane complex (147 mg, 0.179 mmol) was added and the reaction mixture heated by microwave irradiation at 150° C. during 1 hour. The reaction mixture was concentrated and the obtained residue was partitioned between dichloromethane (50 mL) and water (50 mL). The organic layer was separated, dried over magnesium sulphate, filtered and concentrated. The obtained residue was purified by silica gel column chromatography using a gradient from 10 to 100% EtOAc in heptane. The product fractions were concentrated and dried in vacuo overnight at 50° C. yielding compound 7 as a beige powder (208 mg). Method A; Rt: 1.68 min. m/z: 398.9 $(M+H)^+$ Exact mass: 398.1. $^1$H NMR (400 MHz, DMSO-$d_6$) δ ppm 1.65-1.76 (m, 1H), 1.94-2.06 (m, 1H), 2.23 (d, J=1.1 Hz, 3H), 2.71 (s, 3H), 3.44 (dd, J=8.9, 4.3 Hz, 1H), 3.62 (td, J=8.1, 5.9 Hz, 1H), 3.67-3.86 (m, 3H), 7.11 (t, J=9.1 Hz, 1H), 7.52 (dt, J=7.6, 4.0 Hz, 1H), 7.63 (dd, J=6.9, 2.1 Hz, 1H), 7.99 (s, 1H), 8.21 (d, J=6.4 Hz, 1H), 10.12 (s, 1H).

Compound 8: N-(4-fluoro-3-methyl-phenyl)-4-[[(3S)-tetrahydrofuran-3-yl]sulfamoyl]thiophene-2-carboxamide

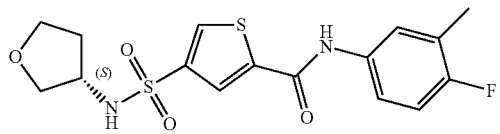

Compound 8 was synthesized similar as described for compound 1, starting from 4-chlorosulfonylthiophene-2-carboxylic acid (commercial from Enamine, EN300-40927) instead of 5-(chlorosulfonyl)-3-thiophenecarboxylic acid. After work up, the obtained residue containing compound 8, was crystallised from hot iPrOH (100 mL) by slow addition of water and stirring overnight. The dark purple crystals were filtered off and purified by silica gel column chromatography on silica using a gradient from 20 till 100% EtOAc in heptane. The product fractions were concentrated and dried in vacuo at 60° C. yielding compound 8 as a beige powder (352.7 mg). Method A; Rt: 1.62 min. m/z: 385.0

(M+H)⁺ Exact mass: 384.1. ¹H NMR (400 MHz, DMSO-d₆) δ ppm 1.61-1.73 (m, 1H), 1.93-2.05 (m, 1H), 2.24 (d, J=1.8 Hz, 3H), 3.40 (dd, J=8.9, 4.5 Hz, 1H), 3.62 (td, J=8.0, 5.9 Hz, 1H), 3.67-3.76 (m, 2H), 3.77-3.86 (m, 1H), 7.14 (t, J=9.1 Hz, 1H), 7.50-7.58 (m, 1H), 7.63 (dd, J=7.0, 2.4 Hz, 1H), 8.02 (d, J=6.6 Hz, 1H), 8.27 (d, J=1.3 Hz, 1H), 8.40 (d, J=1.3 Hz, 1H), 10.47 (s, 1H).

Compound 9: N-(4-fluoro-3-methyl-phenyl)-5-methyl-4-[[(3S)-tetrahydrofuran-3-yl]-sulfamoyl]thiophene-2-carboxamide

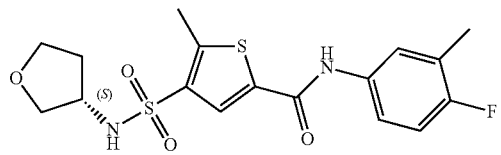

Compound 9 was synthesized similarly as described for compound 1, starting from 4-chlorosulfonyl-5-methyl-thiophene-2-carboxylic acid (commercial from Enamine, EN300-69759) instead of 5-(chlorosulfonyl)-3-thiophenecarboxylic acid. The volatiles of the reaction mixture were removed under reduced pressure and the obtained residue containing compound 9 was purified on silica by gradient elution with a heptane to EtOAc gradient. The product fractions were evaporated to dryness, resulting in compound 9 as a powder (389 mg). Method B; Rt: 0.94 min. m/z: 397.0 (M−H)⁻ Exact mass: 398.1. ¹H NMR (400 MHz, DMSO-d₆) ppm 1.61-1.74 (m, 1H), 1.92-2.04 (m, 1H), 2.24 (d, J=1.5 Hz, 3H), 2.69 (s, 3H), 3.41 (dd, J=9.0, 4.6 Hz, 1H), 3.62 (td, J=8.1, 6.1 Hz, 1H), 3.66-3.76 (m, 2H), 3.76-3.85 (m, 1H), 7.12 (t, J=9.2 Hz, 1H), 7.51-7.59 (m, 1H), 7.63 (dd, J=7.0, 2.4 Hz, 1H), 8.04 (d, J=7.0 Hz, 1H), 8.22 (s, 1H), 10.39 (s, 1H).

Compound 10: N-(4-fluoro-3-methyl-phenyl)-5-methyl-4-[(3-methyloxetan-3-yl)-sulfamoyl]thiophene-2-carboxamide

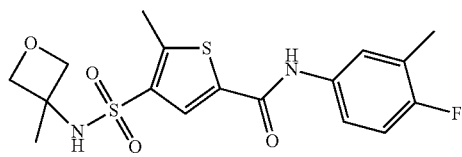 [SMILES: Cc1cc(NC(=O)c2cc(S(=O)(=O)NC3(C)COC3)c(C)s2)ccc1F]

Compound 10 was synthesized similarly as described for compound 9, using 3-methyl-3-oxetanamine hydrochloride (1:1) instead of (S)-(−)-3-aminotetrahydrofuran p-toluenesulfonate, resulting in compound 10 (420 mg) as a powder. Method B; Rt: 0.95 min. m/z: 416.2 (M+NH₄)⁺ Exact mass: 398.1. ¹H NMR (400 MHz, DMSO-d₆) δ ppm 1.49 (s, 3H), 2.24 (d, J=1.6 Hz, 3H), 2.69 (s, 3H), 4.19 (d, J=6.5 Hz, 2H), 4.63 (d, J=6.5 Hz, 2H), 7.12 (t, J=9.3 Hz, 1H), 7.55 (ddd, J=8.8, 4.5, 2.8 Hz, 1H), 7.62 (dd, J=7.1, 2.6 Hz, 1H), 8.23 (s, 1H), 8.40 (s, 1H), 10.38 (s, 1H).

Compound 11: N-(4-fluoro-3-methyl-phenyl)-3-methyl-4-[[(3S)-tetrahydrofuran-3-yl]-sulfamoyl]thiophene-2-carboxamide

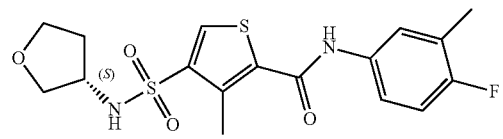

Compound 11 was synthesized similarly as described for compound 9, starting from 4-chlorosulfonyl-3-methyl-thiophene-2-carboxylic acid instead of 4-chlorosulfonyl-5-methyl-thiophene-2-carboxylic acid, resulting in compound 11 (523 mg). Method B; Rt: 0.90 min. m/z: 416.3 (M+NH₄)⁺ Exact mass: 398.1. ¹H NMR (400 MHz, DMSO-d₆) δ ppm 1.65-1.76 (m, 1H), 1.91-2.03 (m, 1H), 2.23 (d, J=1.8 Hz, 3H), 2.53 (s, 3H), 3.42 (dd, J=8.9, 4.5 Hz, 1H), 3.57-3.69 (m, 2H), 3.70-3.80 (m, 2H), 7.12 (t, J=9.2 Hz, 1H), 7.45-7.53 (m, 1H), 7.58 (dd, J=7.0, 2.4 Hz, 1H), 8.13 (d, J=5.7 Hz, 1H), 8.31 (s, 1H), 10.27 (s, 1H).

Compound 12: N-(4-fluoro-3-methyl-phenyl)-3-methyl-4-[(3-methyloxetan-3-yl)-sulfamoyl]thiophene-2-carboxamide

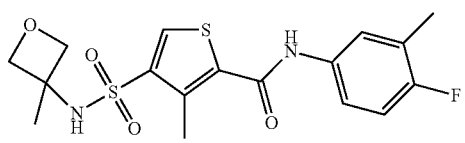 [SMILES: Cc1cc(NC(=O)c2scc(S(=O)(=O)NC3(C)COC3)c2C)ccc1F]

Compound 12 was synthesized similarly as described for compound 11, using 3-methyl-3-oxetanamine hydrochloride (1:1) instead of (S)-(−)-3-aminotetrahydrofuran p-toluenesulfonate, resulting in compound 12 (462 mg). Method B; Rt: 0.91 min. m/z: 416.3 (M+NH₄)⁺ Exact mass: 398.1. ¹H NMR (400 MHz, DMSO-d₆) δ ppm 1.50 (s, 3H), 2.24 (s, 3H), 2.56 (s, 3H), 4.18 (d, J=6.1 Hz, 2H), 4.63 (d, J=6.1 Hz, 2H), 7.12 (t, J=9.3 Hz, 1H), 7.49 (ddd, J=8.8, 4.3, 2.6 Hz, 1H), 7.59 (dd, J=6.9, 2.4 Hz, 1H), 8.33 (s, 1H), 8.44 (s, 1H), 10.28 (s, 1H).

Compound 13: N-(4-fluoro-3-methyl-phenyl)-5-[[(3S)-tetrahydrofuran-3-yl]-sulfamoyl]thiophene-2-carboxamide

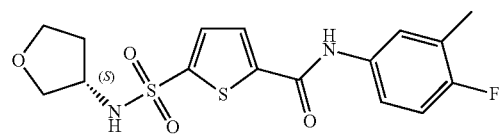

Compound 13 was synthesized similar as described for compound 1, starting from 5-(chlorosulfonyl)-2-thiophenecarboxylic acid (commercial from Enamine: EN300-

95666) instead of 5-(chlorosulfonyl)-3-thiophenecarboxylic acid. After removal of the volatiles of the reaction mixture, CH$_2$Cl$_2$ (150 mL) was added and the mixture was washed with 1 M HCl (2×150 mL) and water (1×150 mL). Compound 13 precipitated from the organic layer and was filtered off. Compound 13 was recrystallised by slow addition of H$_2$O to a solution in methanol (50 mL). The crystals were filtered off and dried in vacuo at 50° C. yielding compound 13 (781 mg) as a light grey powder. Method A; Rt: 1.64 min. m/z: 401.9 (M+NH$_4$)$^+$ Exact mass: 384.1. $^1$H NMR (400 MHz, DMSO-d$_6$) δ ppm 1.62-1.74 (m, 1H), 1.93-2.05 (m, 1H), 2.25 (d, J=1.8 Hz, 3H), 3.42 (dd, J=8.9, 4.3 Hz, 1H), 3.62 (td, J=8.1, 5.7 Hz, 1H), 3.66-3.78 (m, 2H), 3.80-3.91 (m, 1H), 7.15 (t, J=9.1 Hz, 1H), 7.49-7.57 (m, 1H), 7.62 (dd, J=7.0, 2.4 Hz, 1H), 7.69 (d, J=4.0 Hz, 1H), 8.00 (d, J=4.0 Hz, 1H), 8.38 (d, J=6.6 Hz, 1H), 10.46 (s, 1H).

Compound 14: 2-ethyl-N-(4-fluoro-3-methyl-phenyl)-5-[[(3S)-tetrahydrofuran-3-yl]-sulfamoyl]thiophene-3-carboxamide

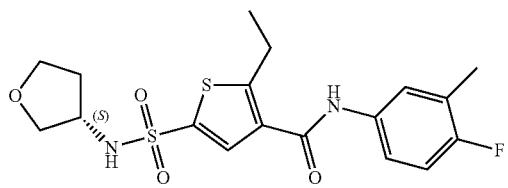

Nitrogen was bubbled through compound 4 (1362 mg, 3.25 mmol), tetraethyltin (0.993 mL, 4.88 mmol), DMF (10 mL) during 5 minutes. 1,1'-bis(diphenylphosphino)ferrocene-palladium(II)dichloride dichloromethane complex (390 mg, 0.477 mmol) was added and the reaction mixture was heated by microwave irradiation at 140° C. during 30 minutes. At room temperature, nitrogen was bubbled through the reaction mixture for 5 minutes, butyldi-1-adamantylphosphine (187 mg, 0.52 mmol) and palladium(II) acetate (73.7 mg, 0.325 mmol) were added and the reaction mixture was further heated by microwave irradiation at 140° C. during 30 minutes and allowed to reach room temperature. The reaction mixture was poured into ice cold water (150 mL). The mixture was filtered and extracted with diethyl ether (3×50 mL). The combined organic layers were washed with Brine, dried (Na$_2$SO$_4$) and concentrated in vacuo, resulting in a dark sticky residue. The water layer was extracted with CH$_2$Cl$_2$ (3×50 mL) and ethyl acetate (3×50 mL). The combined organic layers were dried (Na$_2$SO$_4$) and evaporated to yield a purple liquid which was purified using silica gel column chromatography (ethyl acetate in heptane from 10 to 100%). The desired fractions were evaporated in vacuo until ~20 mL of the solvent remained. The formed solids were filtered, washed with petroleum ether and dried in vacuo at 50° C. resulting in compound 14 as white solid (111 mg). Method B; Rt: 1.00 min. m/z: 430.1 (M+NH$_4$)$^+$ Exact mass: 412.1; $^1$H NMR (400 MHz, DMSO-d$_6$) δ ppm 1.27 (t, J=7.5 Hz, 3H), 1.65-1.76 (m, 1H), 1.94-2.08 (m, 1H), 2.23 (d, J=1.3 Hz, 3H), 3.18 (q, J=7.5 Hz, 2H), 3.44 (dd, J=9.0, 4.4 Hz, 1H), 3.62 (td, J=8.1, 5.8 Hz, 1H), 3.67-3.77 (m, 2H), 3.77-3.87 (m, 1H), 7.11 (t, J=9.2 Hz, 1H), 7.48-7.56 (m, 1H), 7.63 (dd, J=6.9, 2.1 Hz, 1H), 7.99 (s, 1H), 8.21 (br. d, J=6.4 Hz, 1H), 10.15 (br. s, 1H).

Compound 15: N-(4-fluoro-3-methyl-phenyl)-2-methyl-5-[(3-methyloxetan-3-yl)-sulfamoyl]thiophene-3-carboxamide

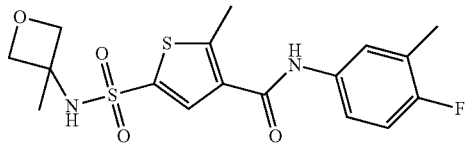 [SMILES: Cc1cc(NC(=O)c2cc(S(=O)(=O)NC3(C)COC3)sc2C)ccc1F]

2-methylthiophene-3-carboxylic acid (15 g, 105.5 mmol) was added portion wise over a period of 15 minutes to chlorosulfonic acid (60 mL) and stirred 2 hours at 100° C. This mixture was allowed to cool 15 minutes and added drop wise during 30 minutes to an ice/water mixture (1500 mL) and stirred for 5 minutes. The brown precipitate was filtered off, rinsed with plenty of water and dried over weekend in a vacuum oven at 50° C., yielding 5-chlorosulfonyl-2-methyl-thiophene-3-carboxylic acid (20.15 g). $^1$H NMR (400 MHz, acetonitrile-d$_3$) δ ppm 2.80 (s, 3H), 8.15 (s, 1H). 5-chlorosulfonyl-2-methyl-thiophene-3-carboxylic acid (20.15 g, 83.72 mmol) was suspended in dichloromethane (500 mL). N,N-dimethylformamide (50 mg) was added followed by portion wise addition of oxalyl chloride (35.42 mL, 418.59 mmol) dissolved in dichloromethane (50 mL). The reaction mixture was stirred for 5 hours and concentrated in vacuo at 50° C. yielding 5-chlorosulfonyl-2-methyl-thiophene-3-carbonyl chloride as a brown residue (21.7 g). $^1$H NMR (400 MHz, chloroform-d) δ ppm 2.84 (s, 3H), 8.31 (s, 1H). 4-fluoro-3-methylaniline (711.6 mg, 5.69 mmol) dissolved in toluene (10 mL) was added drop wise to a solution of 5-chlorosulfonyl-2-methyl-thiophene-3-carbonyl chloride (1473.5 mg, 5.69 mmol) in toluene (90 mL) at reflux during 5 minutes. The mixture was refluxed for 60 minutes and allowed to reach room temperature. A solution of 3-methyl-3-oxetanamine hydrochloride (1:1) (773 mg, 6.25 mmol), diisopropylethylamine (2.84 mL, 16.49 mmol) in dichloromethane (20 mL) was added and the mixture was stirred overnight. The mixture was concentrated in vacuo and the residue was dissolved in EtOAc (200 mL), washed twice with 1M HCl (2×300 mL), once with water (300 mL) and once with saturated NaHCO$_3$ solution. The organic was dried over MgSO$_4$, filtered and concentrated in vacuo. The residue was purified by column chromatography using a gradient from 20% to 100% EtOAc in heptanes. The product fractions were concentrated and the obtained residue crystallized from hot EtOAc (200 mL) upon addition of heptane. The white crystals were filtered off and dried at 50° C. in vacuo yielding compound 15 (805 mg). Method A; Rt: 1.72 min. m/z: 396.9 (M−H)$^−$ Exact mass: 398.1; $^1$H NMR (400 MHz, DMSO-d$_6$) δ ppm 1.55 (s, 3H), 2.23 (d, J=1.8 Hz, 3H), 2.71 (s, 3H), 4.19 (d, J=6.4 Hz, 2H), 4.61 (d, J=5.9 Hz, 2H), 7.11 (t, J=9.2 Hz, 1H), 7.47-7.56 (m, 1H), 7.63 (dd, J=7.0, 2.4 Hz, 1H), 7.99 (s, 1H), 8.61 (s, 1H), 10.11 (s, 1H).

Compound 16: N-(4-fluoro-3-methyl-phenyl)-2-methyl-5-[(3-methyltetrahydrofuran-3-yl)sulfamoyl]thiophene-3-carboxamide

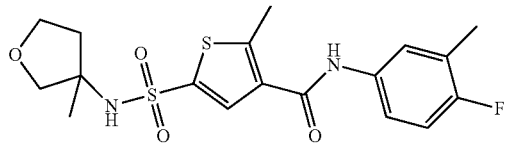 [SMILES: Cc1cc(NC(=O)c2cc(S(=O)(=O)NC3(C)CCOC3)sc2C)ccc1F]

4-fluoro-3-methylaniline (304.98 mg, 2.44 mmol) dissolved in toluene (10 mL) was added drop wise to a solution of 5-chlorosulfonyl-2-methyl-thiophene-3-carbonyl chloride (631.5 mg, 2.44 mmol) in toluene (90 mL) at reflux over a period of 5 minutes. The mixture was refluxed for 60 minutes and allowed to reach room temperature. A solution of 3-methyloxolan-3-amine hydrochloride (368.9 mg, 2.68 mmol) and diisopropylethylamine (1.22 mL, 7.07 mmol) in dichloromethane (8 mL) was added and the mixture was stirred overnight. The mixture was concentrated in vacuo. The residue was dissolved in EtOAc (150 mL), washed twice with 1M HCl (150 mL), once with water (150 mL) and once with saturated NaHCO₃ solution. The organic layer was dried over MgSO₄, filtered and concentrated. The residue was purified by silicagel column chromatography using a gradient from 10% to 100% EtOAc in heptane. The residue was purified again by silicagel column chromatography using a gradient from 0% to 10% methanol in dichloromethane yielding compound 16 as a white resin. Method A; Rt: 1.78 min. m/z: 410.9 (M−H)⁻ Exact mass: 412.1; ¹H NMR (400 MHz, DMSO-d₆) δ ppm 1.31 (s, 3H), 1.78 (dt, J=12.7, 7.6 Hz, 1H), 2.14-2.22 (m, 1H), 2.23 (d, J=1.5 Hz, 3H), 2.70 (s, 3H), 3.40 (d, J=8.8 Hz, 1H), 3.67-3.81 (m, 3H), 7.11 (t, J=9.2 Hz, 1H), 7.47-7.56 (m, 1H), 7.63 (dd, J=7.0, 2.2 Hz, 1H), 7.98 (s, 1H), 8.16 (s, 1H), 10.10 (s, 1H). Racemic N-(4-fluoro-3-methyl-phenyl)-2-methyl-5-[(3-methyltetrahydrofuran-3yl)sulfamoyl]thiophene-3-carboxamide (366 mg) was separated in its two enantiomers by Preparative SFC (Stationary phase: Chiralpak Diacel AD 30×250 mm), Mobile phase: CO₂, MeOH with 0.2% iPrNH₂), the desired fractions were collected, evaporated, dissolved in MeOH and evaporated again. Then this was dried in a vacuum oven at 50° C. overnight yielding enantiomer 16a (166 mg).
and enantiomer 16b (162 mg). Columns: AD-H 250 mm×4.6 mm, Flow: 5 mL/min, Mobile phase: 40% MeOH (containing 0.2% iPrNH₂) hold 4.0, up to 50% in 1 min and hold for 2.0 min @ 50%, Rt: 16a: 1.8 min, 16b: 3.4 min.

Compound 17: 5-(tert-butylsulfamoyl)-N-(3,4-difluorophenyl)-2-methyl-thiophene-3-carboxamide

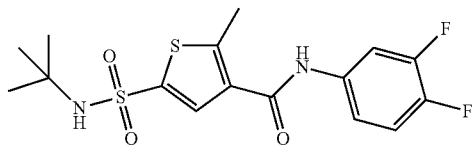 [SMILES: Cc1sc(S(=O)(=O)NC(C)(C)C)cc1C(=O)Nc1ccc(F)c(F)c1]

5-chlorosulfonyl-2-methyl-thiophene-3-carbonyl chloride (2.4 g, 9.26 mmol) was dissolved in toluene (75 mL) and brought to reflux. 3,4-difluoroaniline (1.2 g, 9.26 mmol) was added drop wise in 2 minutes. After addition the reaction was refluxed for 5 hours. The reaction mixture was allowed to reach room temperature and the formed precipitate was filtered off yielding 4-[(3,4-difluorophenyl)carbamoyl]-5-methyl-thiophene-2-sulfonyl chloride (2.1 g). The filtrate was evaporated to dryness yielding another crop of 4-[(3,4-difluorophenyl)carbamoyl]-5-methyl-thiophene-2-sulfonyl chloride (1.2 g). This crop (1.2 g) was dissolved in acetonitrile (10 mL) and treated with tert-butylamine (0.98 mL, 9.26 mmol). The reaction mixture was stirred overnight. The volatiles were removed under reduced pressure and the residue was purified on silica using a heptane to EtOAc gradient yielding compound 17 as a white powder (440.5 mg). Method B; Rt: 1.11 min. m/z: 387.2 (M−H)⁻ Exact mass: 388.1; ¹H NMR (400 MHz, DMSO-d₆) δ ppm 1.19 (s, 9H), 2.70 (s, 3H), 7.36-7.46 (m, 1H), 7.46-7.51 (m, 1H), 7.79 (s, 1H), 7.87 (ddd, J=13.3, 7.5, 2.5 Hz, 1H), 7.95 (s, 1H), 10.32 (s, 1H).

Compound 18: N-(3,4-difluorophenyl)-2-methyl-5-[[(1R)-1-methylpropyl]sulfamoyl]thiophene-3-carboxamide

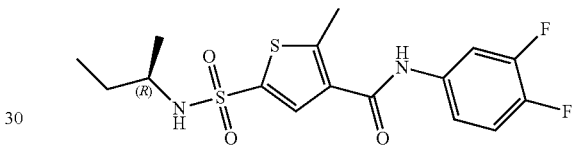

4-[(3,4-difluorophenyl)carbamoyl]-5-methyl-thiophene-2-sulfonyl chloride (500 mg, 1.29 mmol) was dissolved in acetonitrile (10 mL) together with (R)-(−)-2-aminobutane (169.3 mg, 2.32 mmol) and diisopropylethylamine (1.2 mL, 6.95 mmol). The reaction mixture was stirred overnight. The volatiles were removed under reduced pressure and the residue was purified on silicagel using a heptane to EtOAc gradient. The obtained fractions were purified again on silicagel using a heptane to EtOAc gradient yielding compound 18 as a white powder (225 mg). Method B; Rt: 1.11 min. m/z: 387.1 (M−H)⁻ Exact mass: 388.1; ¹H NMR (400 MHz, DMSO-d₆) δ ppm 0.77 (t, J=7.5 Hz, 3H), 0.98 (d, J=6.6 Hz, 3H), 1.37 (quin, J=7.2 Hz, 2H), 2.71 (s, 3H), 3.12-3.23 (m, 1H), 7.36-7.46 (m, 1H), 7.46-7.52 (m, 1H), 7.78-7.92 (m, 2H), 7.97 (s, 1H), 10.32 (s, 1H).

Synthesis of 3-chloro-4,5-difluoro-aniline 3-chloro-4,5-difluorobenzoic acid (1011 mg, 52.5 mmol) was dissolved in tert-butyl alcohol (200 mL). Triethylamine (8 mL, 57.8 mmol) was added followed by diphenylphosphoryl azide (14.74 g, 53.6 mmol) and the reaction mixture was refluxed overnight. The reaction mixture was concentrated and purified by column chromatography on silica using a gradient from 10 to 100% EtOAc in heptane and again with 10% CH₂Cl₂ in heptane to 100% CH₂Cl₂. The product fractions were concentrated in vacuo yielding tert-butyl N-(3-chloro-4,5-difluoro-phenyl)carbamate as a white powder (10.68 g). Method A. Rt: 2.09 min m/z: 262.0 (M−H) Exact mass: 263.1. ¹H NMR (400 MHz, DMSO-d₆) δ ppm 1.48 (s, 9H), 7.37-7.57 (m, 2H), 9.74 (s, 1H). HCl (6 M in iPrOH) (20 mL, 120 mmol) was added to tert-butyl N-(3-chloro-4,5-difluoro-phenyl)carbamate (10.68 g, 40.5 mmol) dissolved in dichloromethane (200 mL) and stirred overnight. The reaction mixture was concentrated. The white solid residue was dissolved in water (100 mL), alkalanised with NaOH 1M and extracted with ether. The organic layer was dried over MgSO$_4$, filtered and concentrated yielding 3-chloro-4,5-difluoro-aniline (6.53 g) as a colorless oil which was stored under nitrogen in the dark. $^1$H NMR (400 MHz, DMSO-d$_6$) δ ppm 5.53 (s, 2H), 6.34-6.61 (m, 2H).

Compound 19: N-(3-chloro-4,5-difluoro-phenyl)-2-methyl-5-[(3-methyloxetan-3-yl)-sulfamoyl]thiophene-3-carboxamide

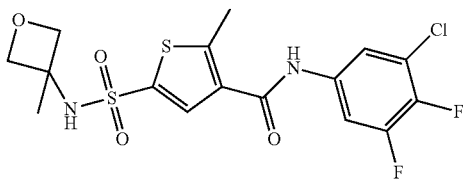 [SMILES: Cc1sc(S(=O)(=O)NC2(C)COC2)cc1C(=O)Nc1cc(F)c(F)c(Cl)c1]

5-chlorosulfonyl-2-methyl-thiophene-3-carbonyl chloride (2.4 g, 9.26 mmol) was dissolved in toluene (75 mL) and brought to reflux. 3-chloro-4,5-difluoro-aniline (1.51 g, 9.26 mmol) was added drop wise in 2 minutes. After addition the reaction was refluxed for 5 hours. The reaction mixture was allowed to reach room temperature and the formed precipitate was filtered off yielding 4-[(3-chloro-4,5-difluoro-phenyl)carbamoyl]-5-methyl-thiophene-2-sulfonyl chloride (2.5 g).

The filtrate was evaporated to dryness yielding another crop of 4-[(3-chloro-4,5-difluoro-phenyl)carbamoyl]-5-methyl-thiophene-2-sulfonyl chloride (1.1 g).

4-[(3-chloro-4,5-difluoro-phenyl)carbamoyl]-5-methyl-thiophene-2-sulfonyl chloride (500 mg) was dissolved in acetonitrile (10 mL) together with 3-methyl-3-oxetanamine (201.72 mg, 2.32 mmol) and diisopropylethylamine (1.2 mL, 6.95 mmol). The reaction mixture was stirred overnight. The volatiles were removed under reduced pressure and the residue was purified using silicagel column chromatography using a heptane to EtOAc gradient. The collected fractions were concentrated under reduced pressure and purified again using silicagel column chromatography using a heptane to EtOAc gradient yielding compound 19 (409 mg) as a white powder. Method B; Rt: 1.08 min. m/z: 435.1 (M−H)$^-$ Exact mass: 436.0; $^1$H NMR (400 MHz, DMSO-d$_6$) δ ppm 1.55 (s, 3H), 2.72 (s, 3H), 4.19 (d, J=6.4 Hz, 2H), 4.61 (d, J=6.2 Hz, 2H), 7.75-7.86 (m, 2H), 8.01 (s, 1H), 8.65 (s, 1H), 10.40 (s, 1H).

Compound 20: 5-(tert-Butylsulfamoyl)-N-(3-chloro-4,5-difluorophenyl)-2-methylthiophene-3-carboxamide

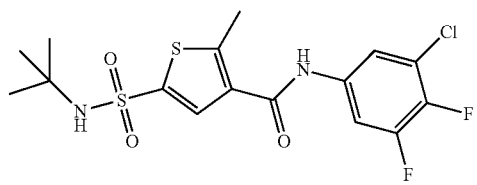 [SMILES: Cc1sc(S(=O)(=O)NC(C)(C)C)cc1C(=O)Nc1cc(F)c(F)c(Cl)c1]

4-[(3-chloro-4,5-difluoro-phenyl)carbamoyl]-5-methyl-thiophene-2-sulfonyl chloride (1.1 g) was dissolved in of acetonitrile (10 mL). This was treated with tert-butylamine (0.98 mL, 9.26 mmol). The reaction mixture was stirred overnight. The volatiles were removed under reduced pressure and the residue was purified using silicagel column chromatography using a heptane to EtOAc gradient yielding compound 20 as a white powder (162 mg). Method B; Rt: 1.24 min. m/z: 421.1 (M−H)$^-$ Exact mass: 422.0; $^1$H NMR (400 MHz, DMSO-d$_6$) δ ppm 1.20 (s, 9H), 2.71 (s, 3H), 7.76-7.87 (m, 3H), 7.97 (s, 1H), 10.38 (br. s., 1H).

Compound 21: 5-(tert-butylsulfamoyl)-2-methyl-N-[3-(trifluoromethyl)phenyl]thiophene-3-carboxamide

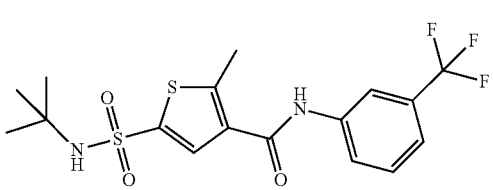 [SMILES: Cc1sc(S(=O)(=O)NC(C)(C)C)cc1C(=O)Nc1cccc(C(F)(F)F)c1]

5-chlorosulfonyl-2-methyl-thiophene-3-carbonyl chloride (2.4 g, 9.26 mmol) was dissolved in toluene (75 mL) and brought to reflux. 3-(trifluoromethyl) aniline (1.15 mL, 9.26 mmol) was added drop wise in 2 minutes. After addition the reaction was refluxed for 2 hours. The reaction mixture was allowed to reach room temperature and the formed precipitate was filtered off yielding 5-methyl-4-[[3-(trifluoromethyl)phenyl]carbamoyl]thiophene-2-sulfonyl chloride (2.87 g).

The filtrate was evaporated to dryness yielding another crop of 5-methyl-4-[[3-(trifluoro-methyl)phenyl]carbamoyl] thiophene-2-sulfonyl chloride (0.5 g). This was dissolved in dichloromethane (20 mL) and tert-butylamine (677.4 mg, 9.26 mmol) was added and the reaction mixture was stirred for 15 minutes. The volatiles were removed under reduced pressure and the residue was purified using silicagel column chromatography using a heptane to EtOAc gradient. The collected fractions were concentrated under reduced pressure and purified again using silicagel column chromatography using a heptane to EtOAc yielding compound 21 as an off white powder (193 mg). Method A; Rt: 1.96 min. m/z: 419.1 (M−H)$^-$ Exact mass: 420.1; $^1$H NMR (400 MHz, DMSO-d$_6$) δ ppm 1.21 (s, 9H), 2.73 (s, 3H), 7.46 (d, J=7.7 Hz, 1H), 7.59 (t, J=7.9 Hz, 1H), 7.80 (s, 1H), 7.97-8.04 (m, 2H), 8.19 (s, 1H), 10.42 (s, 1H).

Compound 22: 2-methyl-5-[(3-methyloxetan-3-yl) sulfamoyl]-N-[3-(trifluoromethyl)-phenyl]thiophene-3-carboxamide

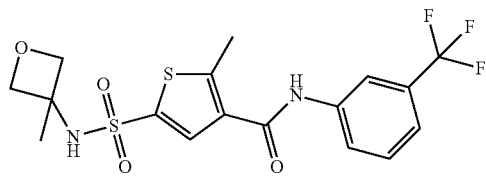 [SMILES: Cc1sc(S(=O)(=O)NC2(C)COC2)cc1C(=O)Nc1cccc(C(F)(F)F)c1]

5-methyl-4-[[3-(trifluoromethyl)phenyl]carbamoyl]thiophene-2-sulfonyl chloride (100 mg) was dissolved in dichloromethane (10 mL). 3-methyl-3-oxetanamine (34.05 mg, 0.39 mmol) and diisopropylethylamine (0.13 mL, 0.78 mmol) were added and the reaction mixture was stirred overnight at room temperature. The precipitate was filtered off, triturated with diisopropylether and dried in a vacuum oven at 50° C. yielding compound 22 (58.5 mg) as a white powder. Method B; Rt: 1.05 min. m/z: 433.1 (M−H)⁻ Exact mass: 434.1; ¹H NMR (400 MHz, DMSO-d₆) δ ppm 1.55 (s, 3H), 2.73 (s, 3H), 4.20 (d, J=6.4 Hz, 2H), 4.61 (d, J=5.9 Hz, 2H), 7.46 (d, J=7.9 Hz, 1H), 7.59 (t, J=7.9 Hz, 1H), 7.98 (d, J=8.6 Hz, 1H), 8.04 (s, 1H), 8.18 (s, 1H), 8.63 (s, 1H), 10.42 (s, 1H).

Synthesis of 3,4-difluoro-5-methyl-aniline 3,4-difluoro-5-methylbenzoic acid (Alfa Aesar, H32313-03, 4.8 g, 26.9 mmol) was dissolved in t-BuOH (100 mL). NEt₃ (4.1 mL, 29.6 mmol) was added followed by diphenylphosphoryl azide (7.5 g, 27.4 mmol) and the reaction mixture was refluxed overnight. The mixture was concentrated and the obtained residue was purified by silica gel column chromatography using a gradient from 30 to 100% EtOAc in heptane. The product fractions were concentrated in vacuo yielding tert-butyl N-(3,4-difluoro-5-methyl-phenyl)carbamate (4.15 g) as a white powder. ¹H NMR (400 MHz, DMSO-d₆) δ ppm 1.47 (s, 9H), 2.22 (d, J=1.8 Hz, 3H), 7.11 (d, J=5.1 Hz, 1H), 7.26-7.38 (m, 1H), 9.47 (br. s., 1H). To a tert-butyl N-(3,4-difluoro-5-methyl-phenyl)carbamate (4.15 g) solution in CH₂Cl₂ (100 mL), HCl (6M in iPrOH, 13.7 mL) was added and the mixture was stirred for 3 hours. The reaction mixture was concentrated in vacuo. The white solid residue was dissolved in water (100 mL), alkalinized with 1M NaOH and extracted with ether. The organic layer was dried over MgSO₄, filtered and concentrated yielding 3,4-difluoro-5-methyl-aniline as a colorless oil which was stored under nitrogen in the dark and used a such. ¹H NMR (400 MHz, DMSO-d₆) δ ppm 2.13 (d, J=2.2 Hz, 3H), 5.11 (s, 2H), 6.16-6.23 (m, 1H), 6.31 (ddd, J=12.9, 6.5, 2.8 Hz, 1H).

Compound 23: 5-(tert-Butylsulfamoyl)-N-(3,4-difluoro-5-methylphenyl)-2-methylthiophene-3-carboxamide

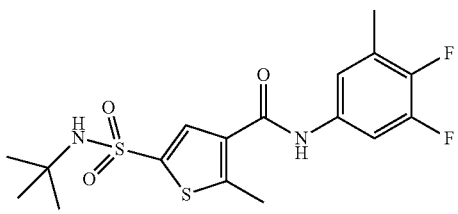 [SMILES: Cc1cc(NC(=O)c2cc(S(=O)(=O)NC(C)(C)C)sc2C)cc(F)c1F]

Compound 23 (221 mg) was prepared similarly as described for compound 17, using 3,4-difluoro-5-methyl-aniline instead of 3,4-difluoroaniline. Method B; Rt: 1.17 min. m/z: 401.1 (M−H)⁻ Exact mass: 402.1. ¹H NMR (400 MHz, DMSO-d₆) δ ppm 1.19 (s, 9H), 2.28 (d, J=2.0 Hz, 3H), 2.70 (s, 3H), 7.40 (d, J=5.9 Hz, 1H), 7.67 (ddd, J=12.8, 7.0, 2.4 Hz, 1H), 7.78 (br. s., 1H), 7.95 (s, 1H), 10.22 (br. s., 1H).

Compound 24: 5-(tert-Butylsulfamoyl)-N-(3-cyano-4-fluorophenyl)-2-methylthiophene-3-carboxamide

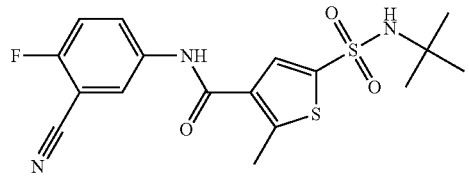 [SMILES: Cc1sc(S(=O)(=O)NC(C)(C)C)cc1C(=O)Nc1ccc(F)c(C#N)c1]

Compound 24 (223 mg) was prepared similarly as described for compound 23, using 5-amino-2-fluoro-benzonitrile instead of 3,4-difluoro-5-methyl-aniline. Method B; Rt: 1.06 min. m/z: 394 (M−H)⁻ Exact mass: 395.1. ¹H NMR (400 MHz, DMSO-d₆) δ ppm 1.20 (s, 9H), 2.71 (s, 3H), 7.54 (t, J=9.2 Hz, 1H), 7.80 (s, 1H), 7.98 (s, 1H), 8.01 (ddd, J=9.2, 4.9, 2.9 Hz, 1H), 8.22 (dd, J=5.8, 2.8 Hz, 1H), 10.44 (s, 1H).

Compound 25: 5-(tert-Butylsulfamoyl)-N-(4-fluoro-3-methylphenyl)-2-methylthiophene-3-carboxamide

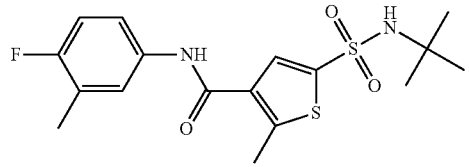 [SMILES: Cc1cc(NC(=O)c2cc(S(=O)(=O)NC(C)(C)C)sc2C)ccc1F]

Compound 25 (158 mg) was prepared similarly as described for compound 23, using 4-fluoro-3-methyl-aniline instead of 3,4-difluoro-5-methyl-aniline. Recrystallized from a MeOH:water mixture, triturated with diisopropylether. Method B; Rt: 1.11 min. m/z: 383 (M−H)⁻ Exact mass: 384.1. ¹H NMR (400 MHz, DMSO-d₆) δ ppm 1.19 (s, 9H), 2.23 (s, 3H), 2.69 (s, 3H), 7.10 (t, J=9.1 Hz, 1H), 7.52 (br. s., 1H), 7.63 (d, J=5.7 Hz, 1H), 7.77 (s, 1H), 7.94 (s, 1H), 10.10 (s, 1H).

Compound 26: 5-(tert-Butylsulfamoyl)-N-(3-chloro-4-fluorophenyl)-2-methylthiophene-3-carboxamide

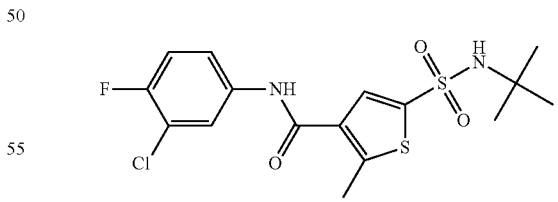

Compound 26 (358 mg) was prepared similarly as described for compound 23, using 3-chloro-4-fluoroaniline instead of 3,4-difluoro-5-methyl-aniline. Recrystallized from a MeOH:water mixture, triturated with diisopropylether. Method B; Rt: 1.17 min. m/z: 403 (M−H)⁻ Exact mass: 404.0. ¹H NMR (400 MHz, DMSO-d₆) δ ppm 1.20 (s, 9H), 2.70 (s, 3H), 7.41 (t, J=9.1 Hz, 1 H), 7.66 (ddd, J=8.9, 4.2, 2.8 Hz, 1H), 7.79 (s, 1H), 7.96 (s, 1H), 8.02 (dd, J=6.8, 2.4 Hz, 1H), 10.29 (s, 1H).

Compound 27: N-(3-Bromo-4-fluorophenyl)-5-(tert-butylsulfamoyl)-2-methylthiophene-3-carboxamide

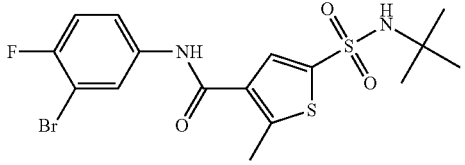 [SMILES: Cc1sc(S(=O)(=O)NC(C)(C)C)cc1C(=O)Nc1ccc(F)c(Br)c1]

Compound 27 (237 mg) was prepared similarly as described for compound 23, using 3-bromo-4-fluoroaniline instead of 3,4-difluoro-5-methyl-aniline. Recrystallized from a MeOH:water mixture, triturated with diisopropylether. Method B; Rt: 1.18 min. m/z: 447 (M−H)⁻ Exact mass: 448.0. $^1$H NMR (400 MHz, DMSO-d$_6$) δ ppm 1.19 (s, 9H), 2.70 (s, 3H), 7.37 (t, J=8.9 Hz, 1H), 7.71 (ddd, J=9.0, 4.5, 2.6 Hz, 1H), 7.78 (s, 1H), 7.96 (s, 1H), 8.13 (dd, J=6.4, 2.6 Hz, 1H), 10.27 (s, 1H). DSC: From 30 to 300° C. at 10° C./min, peak: 192.2° C.

Compound 28: N-(3-Chloro-4-fluorophenyl)-2-methyl-5-[(3-methyloxetan-3-yl)-sulfamoyl]thiophene-3-carboxamide

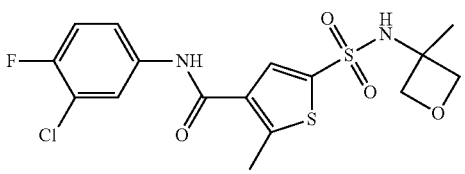 [SMILES: Cc1sc(S(=O)(=O)NC2(C)COC2)cc1C(=O)Nc1ccc(F)c(Cl)c1]

Compound 28 (144 mg) was prepared similarly as described for compound 19, using 3-chloro-4-fluoroaniline instead of 3-chloro-4,5-difluoro-aniline. Method B; Rt: 1.01 min. m/z: 417 (M−H)⁻ Exact mass: 418.0. $^1$H NMR (400 MHz, DMSO-d$_6$) δ ppm 1.55 (s, 3H), 2.71 (s, 3H), 4.19 (d, J=6.6 Hz, 2H), 4.61 (d, J=6.2 Hz, 2H), 7.41 (t, J=9.1 Hz, 1H), 7.59-7.72 (m, 1H), 7.95-8.06 (m, 2H), 8.63 (s, 1H), 10.31 (s, 1H). DSC: From 30 to 300° C. at 10° C./min, peak: 209.9° C.

Compound 29: N-(3-Bromo-4-fluorophenyl)-2-methyl-5-[(3-methyloxetan-3-yl)-sulfamoyl]thiophene-3-carboxamide

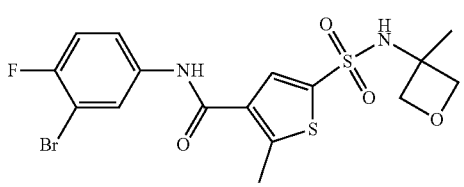 [SMILES: Cc1sc(S(=O)(=O)NC2(C)COC2)cc1C(=O)Nc1ccc(F)c(Br)c1]

Compound 29 (146 mg) was prepared similarly as described for compound 19, using 3-bromo-4-fluoroaniline instead of 3-chloro-4,5-difluoro-aniline. Method B; Rt: 1.03 min. m/z: 461 (M−H)⁻ Exact mass: 462.0. $^1$H NMR (400 MHz, DMSO-d$_6$) δ ppm 1.55 (s, 3H), 2.72 (s, 3H), 4.20 (d, J=6.4 Hz, 2H), 4.61 (d, J=6.2 Hz, 2H), 7.35-7.41 (m, 1H), 7.70 (ddd, J=9.0, 4.4, 2.6 Hz, 1H), 8.00 (s, 1H), 8.10-8.15 (m, 1H), 8.63 (s, 1H), 10.29 (s, 1H).

Compound 30: Methyl N-({4-[(3,4-difluorophenyl)carbamoyl]-5-methylthiophen-2-yl}sulfonyl)-2-methylalaninate

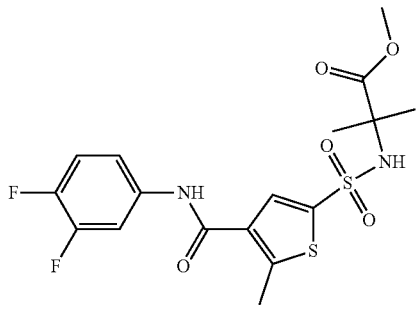 [SMILES: COC(=O)C(C)(C)NS(=O)(=O)c1cc(C(=O)Nc2ccc(F)c(C)c2)c(C)s1]

4-((3,4-difluorophenyl)carbamoyl)-5-methylthiophene-2-sulfonyl chloride (300 mg, 0.853 mmol) was dissolved in CH$_2$Cl$_2$ (10 mL). Methyl 2-amino-2-methylpropanoate hydrochloride (158 mg, 1.03 mmol) and triethylamine (218 mg, 2.15 mmol) were added. The mixture was stirred at room temperature for 2 hours. The reaction mixture was poured into water, and the separated organic layer was washed with water, dried over Na$_2$SO$_4$ and evaporated to dryness resulting in an oil which was purified by preparative high performance liquid chromatography over RP-18 (eluent: CH$_3$CN in H$_2$O (0.1% HCl) from 20% to 60%, v/v). The pure fractions were collected and evaporated to dryness resulting in compound 30 (46.3 mg) as a white solid. Method C; Rt: 5.18 min. m/z: 433 (M+H)⁺ Exact mass: 432.1.

Compound 31: Methyl N-({4-[(4-fluoro-3-methylphenyl)carbamoyl]-5-methylthiophen-2-yl}sulfonyl)-2-methylalaninate

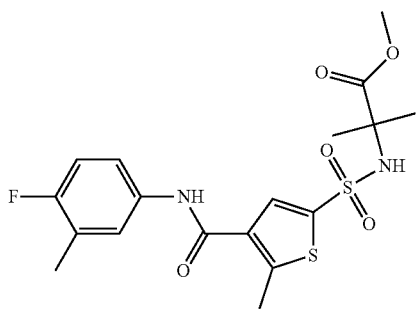

Compound 31 was prepared similarly as described for compound 30 starting from 4-((4-fluoro-3-methylphenyl)carbamoyl)-5-methylthiophene-2-sulfonyl chloride instead of 4-((3,4-difluorophenyl)carbamoyl)-5-methylthiophene-2-sulfonyl chloride. Method C; Rt: 5.17 min. m/z: 429 (M+H)⁺ Exact mass: 428.1.

Compound 32: 5-[(2-Amino-1,1-dimethyl-2-oxo-ethyl)sulfamoyl]-N-(3,4-difluorophenyl)-2-methylthiophene-3-carboxamide

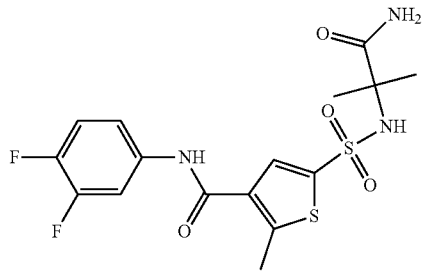 [SMILES: Cc1sc(S(=O)(=O)NC(C)(C)C(N)=O)cc1C(=O)Nc1ccc(F)c(F)c1]

Compound 30 (250 mg, 0.578 mmol) was dissolved in MeOH (5 mL) and H$_2$O (5 mL), LiOH (46 mg, 1.92 mmol) was added. The mixture was stirred at room temperature for 12 hours. The reaction mixture was evaporated to dryness. The mixture was adjusted to pH 3-4 with HCl, and was poured into water (5 mL), and was extracted with ethylacetate (10 mL) twice. The combined organic layers were washed with water and dried over Na$_2$SO$_4$. The organic layers was vaporated to dryness to provide a yellow oil (200 mg). This oil (200 mg, 0.478 mmol) HATU (272 mg, 0.715 mmol) and triethylamine (58 mg, 0.573 mmol) in DMF (5 mL) saturated with ammonia was stirred at room temperature for 2 hours. The reaction mixture was poured into water (3 mL), and was extracted with ethylacetate (2×3 mL). The combined organic layers were washed with water and dried over Na$_2$SO$_4$. The organic layers were evaporated to dryness to provide a yellow oil. The obtained residue was purified by preparative high performance liquid chromatography over RP-18 (eluent: CH$_3$CN in H$_2$O (0.1% FA) from 20% to 60%, v/v). The pure fractions were collected and evaporated to dryness to resulting in compound 32 (35 mg) as a white solid. Method C; Rt: 4.64 min. m/z: 418 (M+H)$^+$ Exact mass: 417.1.

Compound 33: 5-[(2-Amino-1,1-dimethyl-2-oxo-ethyl)sulfamoyl]-N-(4-fluoro-3-methylphenyl)-2-methylthiophene-3-carboxamide

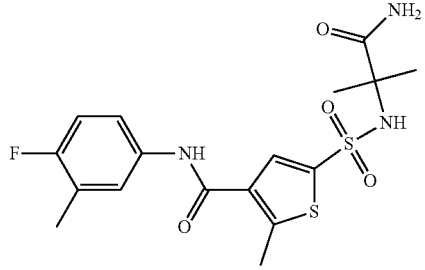

Compound 33 (61 mg) was prepared similarly as described for compound 32, starting from compound 31 instead of compound 30. Method C; Rt: 4.64 min. m/z: 414 (M+H)$^+$ Exact mass: 413.1. $^1$H NMR (400 MHz, DMSO-d$_6$) δ ppm 1.34 (s, 6H) 2.23 (d, J=1.8 Hz, 3H) 2.69 (s, 3H) 7.03-7.17 (m, 3H) 7.45-7.55 (m, 1H) 7.59-7.68 (m, 1H) 7.90-8.03 (m, 2H) 10.10 (s, 1H)

Compound 34: N-(3,4-Difluorophenyl)-2-methyl-5-{[1-(trifluoromethyl)cyclopropyl]-sulfamoyl}thiophene-3-carboxamide

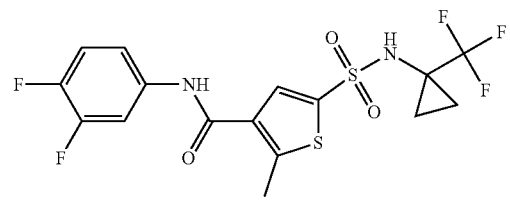

A mixture of 4-((3,4-difluorophenyl)carbamoyl)-5-methylthiophene-2-sulfonyl chloride (100 mg, 0.284 mmol), 1-(trifluoromethyl)cyclopropanamine (40 mg, 0.32 mmol) and pyridine (3 mL) was stirred at 30° C. for 15 minutes. The mixture was concentrated in vacuo. The obtained residue was purified by high performance liquid chromatography (Column: ASBC18 150*25 mm. HCl water B: MeCN.

The product fractions were collected and the organic solvent was evaporated. The fraction was neutralized by saturated NaHCO$_3$. The mixture was extracted with dichloromethane (3×20 mL). The combined organic layers were dried over Na$_2$SO$_4$ and concentrated in vacuo resulting in compound 34 (36 mg). Method C; Rt: 5.51 min. m/z: 441 (M+H)$^+$ Exact mass: 440.0. $^1$H NMR (400 MHz, DMSO-d$_6$) δ ppm 1.06-1.33 (m, 4H) 2.70 (s, 3H) 7.31-7.56 (m, 2H) 7.87 (ddd, J=13.2, 7.5, 2.1 Hz, 1H) 7.99 (s, 1H) 9.43 (s, 1H) 10.37 (s, 1H).

Compound 35: N-(4-Fluoro-3-methylphenyl)-2-methyl-5-{[1-(trifluoromethyl)cyclo-propyl]sulfamoyl}thiophene-3-carboxamide

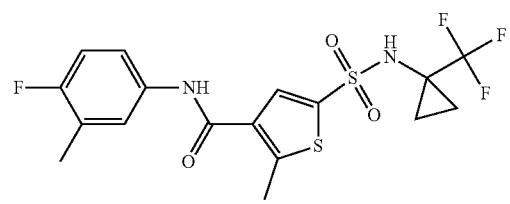 [SMILES: Cc1sc(S(=O)(=O)NC2(C(F)(F)F)CC2)cc1C(=O)Nc1ccc(F)c(F)c1]

Compound 35 (15 mg) was prepared similarly as described for compound 34 starting from 4-((4-fluoro-3-methylphenyl)carbamoyl)-5-methylthiophene-2-sulfonyl chloride instead of 4-((3,4-difluorophenyl)carbamoyl)-5-methylthiophene-2-sulfonyl chloride. Method D; Rt: 4.17 min. m/z: 437 (M+H)$^+$ Exact mass: 436.1. $^1$H NMR (400 MHz, DMSO-d$_6$) δ ppm 1.09-1.30 (m, 4H) 2.23 (d, J=1.5 Hz, 3H) 2.70 (s, 3H) 7.11 (t, J=9.2 Hz, 1H) 7.47-7.57 (m, 1H) 7.59-7.68 (m, 1H) 7.98 (s, 1H) 9.41 (s, 1H) 10.14 (s, 1H).

Compound 36: N-(3-Chloro-4,5-difluorophenyl)-2-methyl-5-{[(1R)-2,2,2-trifluoro-1-methylethyl]sulfamoyl}thiophene-3-carboxamide

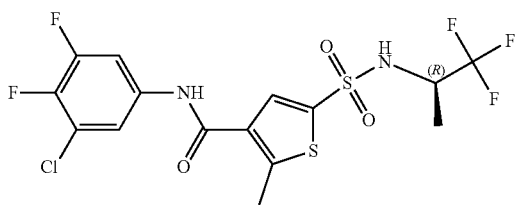

4-[(3-chloro-4,5-difluoro-phenyl)carbamoyl]-5-methyl-thiophene-2-sulfonyl chloride (400 mg, 1.036 mmol, purified via silica gel chromatography) was dispensed in acetonitrile (1 mL) and dried with molecular sieves 4A powder. (R)-1,1,1-trifluoro-2-propylamine (585.6 mg, 5.12 mmol was dissolved in acetonitrile (1 mL) and dried with molecular sieves 4A powder. The solutions were combined and stirred for 3 hours at 80° C. The reaction mixture was filtered and evaporated to dryness. The obtained residue was purified by silica gel chromatography using a heptane to EtOAc gradient resulting in compound 36 (372 mg) as a white powder. Method B; Rt: 1.19 min. m/z: 461 (M–H)⁻ Exact mass: 462.0. $^1$H NMR (400 MHz, DMSO-d$_6$) δ ppm 1.09 (d, J=7.0 Hz, 3H), 2.73 (s, 3H), 4.01-4.13 (m, 1H), 7.75-7.86 (m, 2H), 8.07 (s, 1H), 8.86 (d, J=7.9 Hz, 1H), 10.41 (s, 1H).

Compound 37: N-(3-Chloro-4,5-difluorophenyl)-2-methyl-5-{[(1S)-2,2,2-trifluoro-1-methylethyl]sulfamoyl}thiophene-3-carboxamide

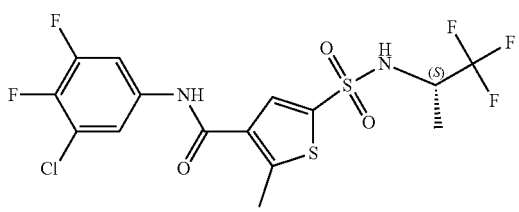

Compound 37 (48 mg) was prepared similarly as described for compound 36, using (S)-1,1,1-trifluoro-2-propylamine instead of (R)-1,1,1-trifluoro-2-propylamine.

Method B; Rt: 1.19 min. m/z: 461 (M–H)⁻ Exact mass: 462.0. $^1$H NMR (400 MHz, DMSO-d$_6$) δ ppm 1.09 (d, J=7.0 Hz, 3H), 2.73 (s, 3H), 3.98-4.14 (m, 1H), 7.73-7.87 (m, 2H), 8.07 (s, 1H), 8.86 (d, J=8.6 Hz, 1H), 10.41 (s, 1H).

Compound 38: N-(3-Chloro-4-fluorophenyl)-2-methyl-5-{[(1R)-2,2,2-trifluoro-1-methylethyl]sulfamoyl}thiophene-3-carboxamide

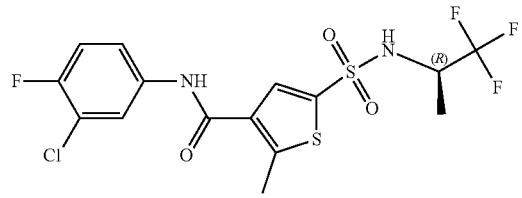

Compound 38 (223 mg) was prepared similarly as described for compound 36, using 4-[(3-chloro-4-fluorophenyl)carbamoyl]-5-methyl-thiophene-2-sulfonyl chloride instead of 4-[(3-chloro-4,5-difluoro-phenyl)carbamoyl]-5-methyl-thiophene-2-sulfonyl chloride, stirring overnight at 80° C. Method B; Rt: 1.13 min. m/z: 443 (M–H)⁻ Exact mass: 444.0. $^1$H NMR (400 MHz, DMSO-d$_6$) δ ppm 1.09 (d, J=6.8 Hz, 3H), 2.72 (s, 3H), 3.99-4.16 (m, 1H), 7.42 (t, J=9.1 Hz, 1H), 7.66 (ddd, J=9.0, 4.4, 2.6 Hz, 1H), 8.02 (dd, J=6.9, 2.5 Hz, 1H), 8.07 (s, 1H), 8.84 (d, J=8.1 Hz, 1H), 10.31 (s, 1H).

Compound 39: N-(4-Fluoro-3-methylphenyl)-2-methyl-5-{[(1R)-2,2,2-trifluoro-1-methylethyl]sulfamoyl}thiophene-3-carboxamide

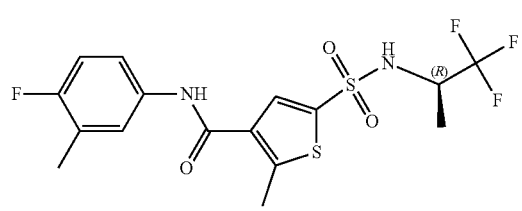

Compound 39 (18 mg) was prepared similarly as described for compound 36, starting from 4-((4-fluoro-3-methylphenyl)carbamoyl)-5-methylthiophene-2-sulfonyl chloride instead of 4-[(3-chloro-4,5-difluoro-phenyl)carbamoyl]-5-methyl-thiophene-2-sulfonyl chloride. Method B; Rt: 1.09 min. m/z: 423 (M–H)⁻ Exact mass: 424.1. $^1$H NMR (400 MHz, DMSO-d$_6$) δ ppm 1.09 (d, J=6.8 Hz, 3H), 2.24 (d, J=1.5 Hz, 3H), 2.71 (s, 3H), 4.07 (dt, J=14.5, 7.2 Hz, 1H), 7.11 (t, J=9.1 Hz, 1H), 7.48-7.56 (m, 1H), 7.63 (dd, J=7.0, 2.4 Hz, 1H), 8.05 (s, 1H), 8.82 (br. s., 1H), 10.11 (s, 1H).

Compound 40: N-(3-chloro-4,5-difluoro-phenyl)-2-methyl-5-[(2,2,2-trifluoro-1,1-dimethyl-ethyl)sulfamoyl]thiophene-3-carboxamide

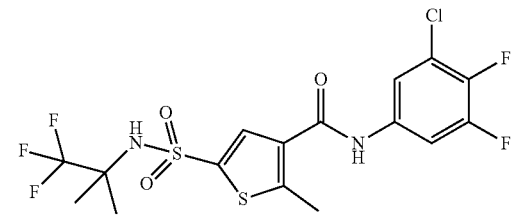 [SMILES: Cc1sc(S(=O)(=O)NC(C)(C)C(F)(F)F)cc1C(=O)Nc1cc(F)c(F)c(Cl)c1]

Compound 40 (37 mg) was prepared similarly as described for compound 36, using 2,2,2-trifluoro-1,1-dimethyl-ethylamine instead of (R)-1,1,1-trifluoro-2-propylamine and stirring at 80° C. overnight, followed by 15 hours more. Method B; Rt: 1.24 min. m/z: 475.0 (M−H)⁻ Exact mass: 476.0. ¹H NMR (400 MHz, DMSO-d₆) δ ppm 1.39 (s, 6H), 2.72 (s, 3H), 7.75-7.86 (m, 2H), 8.01 (s, 1H), 8.73 (br. s., 1H), 10.40 (s, 1H).

Synthesis of
3-(trifluoromethyl)tetrahydrofuran-3-amine hydrochloride

A mixture of 3-oxotetrahydrofuran (30 g, 348.5 mmol), benzylamine (39.2 g, 365.8 mmol), MgSO₄ (21 g, 174.5 mmol) and CH₂Cl₂ (200 mL) was stirred at 28° C. for 24 hours. The mixture was filtered. The filtrate was concentrated in vacuo and the obtained residue (63.1 g) was used directly in the next step. The obtained residue (63 g) was dissolved in acetonitrile (600 mL). Trifluoroacetic acid (45 g, 394 mmol), potassium hydrogenfluoride (22.5 g, 288 mmol) and DMF (60 mL) were added to the mixture at 0° C. The mixture was stirred at 0° for 10 minutes. (trifluoromethyl)trimethylsilane (77 g, 541 mmol) was added to the reaction mixture and the mixture was stirred at ambient temperature for 12 h. Saturated aqueous Na₂CO₃ (200 mL) was added and the mixture was stirred for 5 min. The mixture was diluted with water (500 mL), and extracted with ethyl acetate (3×300 mL). The combined organic layers were washed with water and brine, dried over Na₂SO₄ and evaporated under reduced pressure. The obtained residue was dissolved in 2M HCl/MeOH and the solvent was evaporated. The resulting hydrochloride salt was crystallized from CH₃CN to provide N-benzyl-3-(trifluoromethyl) tetrahydrofuran-3-amine (30.5 g). A mixture of N-benzyl-3-(trifluoromethyl)tetrahydrofuran-3-amine (30.5 g), palladium on alumina (1.5 g) and MeOH was stirred under H₂ (20 psi) atmosphere at 28° C. for 12 hours. The mixture was filtered and the filtrate was concentrated in vacuo resulting in 3-(trifluoromethyl)tetrahydrofuran-3-amine hydrochloride (20.5 g). ¹H NMR (400 MHz, DMSO-d₆) δ ppm 2.21-2.43 (m, 2H) 3.83-4.16 (m, 4H) 9.68 (br. s., 3H).

Compound 41: 2-methyl-N-[3-(trifluoromethyl)phenyl]-5-[[3-(trifluoromethyl)tetrahydrofuran-3-yl]sulfamoyl]thiophene-3-carboxamide

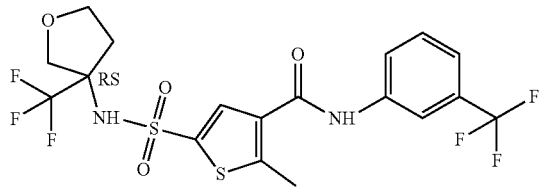 [SMILES: Cc1sc(S(=O)(=O)NC2(C(F)(F)F)CCOC2)cc1C(=O)Nc1cccc(C(F)(F)F)c1]

A solution of 5-methyl-4-[[3-(trifluoromethyl)phenyl]carbamoyl]thiophene-2-sulfonyl chloride (800 mg, 2.08 mmol) in acetonitrile (10 mL) was sonicated for 10 minutes with molecular sieves 5A. A solution of 3-(trifluoromethyl)tetrahydrofuran-3-amine (420 mg) was also treated with molecular sieves in the same way. Both suspensions were then combined and heated 24 hours at 80° C. The mixture was filtered off and the filtrate was concentrated under vacuum. The residue was purified by high performance liquid chromatography (Column: Gemini C18 150*25 mm*10 ul. A: base water B: MeCN. Flow Rate (mL/min): 25). The product fractions were collected and the organic solvent was evaporated. The aqueous layer was freeze-dried to give compound 41 (racemic, 24.1 mg). Method F; Rt: 4.59 min. m/z: 503.2 (M+H)⁺ Exact mass: 502.1. ¹H NMR (400 MHz, DMSO-d₆) δ ppm 10.45 (s, 1H), 9.14 (br. s., 1H), 8.18 (s, 1H), 8.07 (s, 1H), 7.99 (d, J=8.8 Hz, 1H), 7.63-7.56 (m, 1H), 7.46 (d, J=7.8 Hz, 1H), 4.10 (d, J=10.8 Hz, 1H), 3.95 (d, J=10.3 Hz, 1H), 3.85 (m, J=4.5, 8.4 Hz, 1H), 3.61 (m, J=7.6 Hz, 1H), 2.73 (s, 3H), 2.45 (m, J=7.0 Hz, 1H), 2.30-2.20 (m, 1H).

Compound 42: 2-methyl-5-[(2,2,2-trifluoro-1,1-dimethyl-ethyl)sulfamoyl]-N-[3-(trifluoromethyl)phenyl]thiophene-3-carboxamide

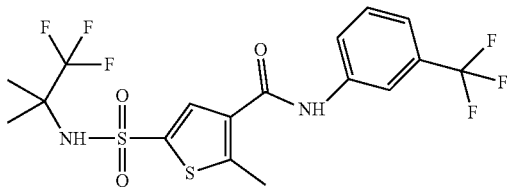 [SMILES: Cc1sc(S(=O)(=O)NC(C)(C)C(F)(F)F)cc1C(=O)Nc1cccc(C(F)(F)F)c1]

Compound 42 (23.4 mg) was prepared similarly as described for compound 41, using only 300 mg of 5-methyl-4-[[3-(trifluoromethyl)phenyl]carbamoyl]thiophene-2-sulfonyl chloride and 2,2,2-trifluoro-1,1-dimethyl-ethylamine (120 mg, 0.94 mmol) instead of 3-(trifluoromethyl)tetrahydrofuran-3-amine. Purification by high performance liquid chromatography (Column: ASB C18 150*25 mm. A: HCl water B: MeCN. Flow Rate (mL/min): 25). Method D; Rt: 4.54 min. m/z: 475.0 (M+H)⁺ Exact mass: 474.1. ¹H NMR (400 MHz, DMSO-d₆) δ ppm 10.48 (s, 1H), 8.74 (br. s., 1H), 8.19 (s, 1H), 8.06 (s, 1H), 7.99 (d, J=8.5 Hz, 1H), 7.59 (t, J=8.0 Hz, 1H), 7.46 (d, J=7.8 Hz, 1H), 2.73 (s, 3H), 1.39 (s, 6H).

Compound 43: N-(3-cyano-4-fluoro-phenyl)-5-[[2-fluoro-1-(fluoromethyl)ethyl]sulfamoyl]-2-methyl-thiophene-3-carboxamide

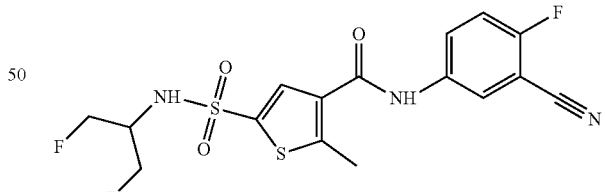

5-chlorosulfonyl-2-methyl-thiophene-3-carbonyl chloride (2 g, 7.72 mmol) was dissolved in toluene (75 mL) and brought to reflux. 5-amino-2-fluorobenzonitrile (1.2 g, 6.41 mmol) was added portion wise in 2 minutes. After addition the reaction was refluxed for 1 hour. The reaction mixture was concentrated in vacuum yielding a crude powder (2.1 g) which was used as such. 4-((3-cyano-4-fluorophenyl)carbamoyl)-5-methylthiophene-2-sulfonyl chloride (500 mg, 1.39 mmol) was dissolved in CH₂Cl₂ (10 mL). 1,3-difluoro-2-propylamine hydrochloride (205 mg, 1.56 mmol) and triethylamine (350 mg, 3.46 mmol) were added and the mixture was stirred at room temperature for 2 hours. The reaction mixture was poured into water, and the separated organic layer was washed with water, dried over Na$_2$SO$_4$ and evaporated to dryness to provide an oil. The residue was purified by preparative high performance liquid chromatography over RP-18 (eluent: CH$_3$CN in H$_2$O (0.1% FA) from 20% to 60%, v/v). The pure fractions were collected and evaporated to dryness to provide compound 43 (133 mg) as a pale yellow solid. Method E; Rt: 5.23 min. m/z: 418.2 (M+H)$^+$ Exact mass: 417.0. $^1$H NMR (400 MHz, DMSO-d$_6$) δ ppm 10.48 (s, 1H), 8.69 (br. s., 1H), 8.23 (dd, J=2.8, 5.8 Hz, 1H), 8.05 (s, 1H), 8.03-7.99 (m, 1H), 7.55 (t, J=9.2 Hz, 1H), 4.48 (dd, J=1.0, 5.3 Hz, 2H), 4.36 (dd, J=1.0, 5.3 Hz, 2H), 3.84-3.68 (m, 1H), 2.72 (s, 3H).

Synthesis of
5-Amino-2-Fluoro-3-Methyl-Benzonitrile 2-fluoro-3-methylbenzonitrile (18 g, 133 mmol) was added to a solution of potassium nitrate (13.5 g, 133 mmol) in sulfuric acid (250 mL) cooled at 0° C., the mixture was allowed to stir at room temperature for 40 minutes. The reaction mixture was poured into ice water and the pale yellow precipitate was filtered off and dried in the vacuum oven yielding crude 2-fluoro-3-methyl-5-nitro-benzonitrile (18 g). Crude 2-fluoro-3-methyl-5-nitro-benzonitrile (18 g) was stirred in MeOH (210 mL) and water (70 mL). Fe powder (16.7 g) and HCl (36 mL, 5 equiv) were added and the mixture was stirred at room temperature for 2 hours. The reaction mixture was then filtered through celite and after removal of organic solvent, the mixture was adjusted to pH 9 with saturated solution of sodium carbonate and extracted with CH$_2$Cl$_2$ twice. The combined organic layers were dried over sodium sulfate and evaporated to dryness to provide a yellow oil. The crude product was purified by column chromatography to provide 5-amino-2-fluoro-3-methyl-benzonitrile (5.1 g) as a pale yellow solid.

Synthesis of 4-[(3-cyano-4-fluoro-5-methyl-phenyl)
carbamoyl]-5-methyl-thiophene-2-sulfonyl chloride 5-chlorosulfonyl-2-methyl-thiophene-3-carbonyl chloride (260 mg, 1 mmol) was dissolved in toluene (5 mL) and brought to reflux. 5-amino-2-fluoro-3-methyl-benzonitrile (150 mg, 1 mmol) was added. After addition the reaction was refluxed for 2 hours. The reaction mixture was concentrated in vacuum yielding a crude powder (400 mg) which was used as such.

Compound 44: N-(3-cyano-4-fluoro-5-methyl-phenyl)-2-methyl-5-[(3-methyloxetan-3-yl)sulfamoyl]thiophene-3-carboxamide

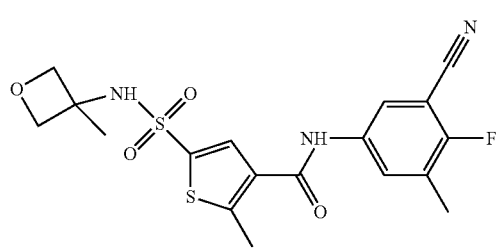 [SMILES: Cc1cc(NC(=O)c2cc(S(=O)(=O)NC3(C)COC3)sc2C)cc(C#N)c1F]

4-[(3-cyano-4-fluoro-5-methyl-phenyl)carbamoyl]-5-methyl-thiophene-2-sulfonyl chloride (175 mg, 0.47 mmol) was dissolved in CH$_2$Cl$_2$ (10 mL). 3-methyloxetan-3-amine (52 mg, 0.6 mmol) and triethylamine (80 mg, 0.79 mmol) were added and the mixture was stirred at room temperature for 2 hours. The reaction mixture was poured into water, and the separated organic layer was washed with water, dried over Na$_2$SO$_4$ and evaporated to dryness to provide an oil. The residue was purified by preparative high performance liquid chromatography over RP-18 (eluent: CH$_3$CN in H$_2$O (0.1% FA) from 20% to 60%, v/v). The pure fractions were collected and evaporated to dryness to provide compound 44 (56.8 mg) as a white solid. Method G; Rt: 4.63 min. m/z: 441.1 (M+NH$_4$)$^+$ Exact mass: 423.1. $^1$H NMR (400 MHz, DMSO-d$_6$) δ ppm 10.37 (s, 1H), 8.65 (s, 1H), 8.04-7.88 (m, 3H), 4.61 (d, J=6.0 Hz, 2H), 4.19 (d, J=6.5 Hz, 2H), 2.72 (s, 3H), 2.30 (d, J=2.0 Hz, 3H), 1.55 (s, 3H).

Compound 45: N-(3-cyano-4-fluoro-phenyl)-2-methyl-5-[(2,2,2-trifluoro-1,1-dimethyl-ethyl)sulfamoyl]thiophene-3-carboxamide

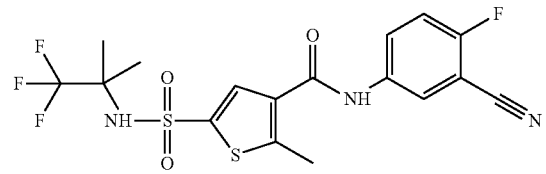 [SMILES: Cc1sc(S(=O)(=O)NC(C)(C)C(F)(F)F)cc1C(=O)Nc1ccc(F)c(C#N)c1]

5-chlorosulfonyl-2-methyl-thiophene-3-carbonyl chloride (1.5 g, 5.79 mmol) was dissolved in toluene (30 mL) and brought to reflux. 5-amino-2-fluorobenzonitrile (790 mg, 5.8 mmol) dissolved in toluene was added drop wise in 10 minutes. After addition the reaction was refluxed for 1 hour. The reaction mixture was concentrated in vacuum yielding a crude powder which was purified via silica gel chromatography using petroleumether:EtOAc 10:1 as eluent yielding 4-[(3-cyano-4-fluoro-phenyl)carbamoyl]-5-methyl-thiophene-2-sulfonyl chloride (1.2 g).

Compound 45 (28.9 mg) was further prepared similarly as described for compound 41, using 100 mg of 4-[(3-cyano-4-fluoro-phenyl)carbamoyl]-5-methyl-thiophene-2-sulfonyl chloride instead of 5-methyl-4-[[3-(trifluoromethyl)phenyl]carbamoyl]thiophene-2-sulfonyl chloride and 2,2,2-trifluoro-1,1-dimethyl-ethylamine (40 mg, 0.31 mmol) instead of 3-(trifluoromethyl)tetrahydrofuran-3-amine. Purification by high performance liquid chromatography (Column: ASB C18 150*25 mm. A: HCl water B: MeCN. Flow Rate (mL/min): 25). Method E; Rt: 5.75 min. m/z: 450.2 (M+H)$^+$ Exact mass: 449.1. $^1$H NMR (400 MHz, DMSO-d$_6$) δ ppm 10.53 (s, 1H), 8.76 (s, 1H), 8.23 (dd, J=2.5, 5.8 Hz, 1H), 8.05-7.98 (m, 2H), 7.54 (t, J=9.2 Hz, 1H), 2.72 (s, 3H), 1.38 (s, 6H).

Compound 46: N-(3-cyano-4-fluoro-phenyl)-2-methyl-5-[[(1S)-2,2,2-trifluoro-1-methyl-ethyl]sulfamoyl]thiophene-3-carboxamide

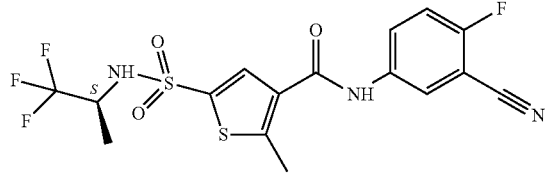

Compound 46 (422.7 mg) was prepared similarly as described for compound 36, starting from 4-[(3-cyano-4-fluoro-phenyl)carbamoyl]-5-methyl-thiophene-2-sulfonyl chloride (500 mg, 1.39 mmol) and using (S)-1,1,1-trifluoro-2-propylamine (473 mg, 4.18 mmol) instead of (R)-1,1,1-trifluoro-2-propylamine. The obtained filtrate was evaporated to dryness and the residue was crystallized from CH$_2$Cl$_2$, triturated with diisopropylether and dried yielding compound 46 as a white powder. Method B; Rt: 1.03 min. m/z: 434 (M−H)$^-$ Exact mass: 435.0. $^1$H NMR (400 MHz, DMSO-d$_6$) δ ppm 1.09 (d, J=6.8 Hz, 3H), 2.73 (s, 3H), 4.01-4.13 (m, 1H), 7.55 (t, J=9.1 Hz, 1H), 8.01 (ddd, J=9.2, 4.9, 2.6 Hz, 1H), 8.08 (s, 1H), 8.22 (dd, J=5.8, 2.8 Hz, 1H), 8.85 (d, J=8.8 Hz, 1H), 10.46 (s, 1H).

Synthesis of 4-[(3,4-difluorophenyl)carbamoyl]-5-methyl-thiophene-2-sulfonyl chloride 5-chlorosulfonyl-2-methyl-thiophene-3-carbonyl chloride (5 g, 19.3 mmol) was dissolved in toluene (20 mL) and brought to reflux. 3,4-difluoroaniline (2.5 g, 19.4 mmol) dissolved in toluene (1 mL) was drop wise during 1 minute. After addition the reaction was refluxed for 2 hours. The reaction mixture was concentrated in vacuum yielding 4-[(3,4-difluorophenyl)carbamoyl]-5-methyl-thiophene-2-sulfonyl chloride as a crude powder (6 g) which was used as such.

Synthesis of (2S)-3,3-difluorobutan-2-amine hydrochloride (S)-2-((tert-butoxycarbonyl)amino)propanoic acid (39 g, 206 mmol), N,O-dimethyl-hydroxylamine hydrochloride (24 g, 246 mmol), HATU (117 g, 308 mmol) and N,N-diisopropylethylamine (66.3 g, 513 mmol) were dissolved in DMF (500 mL) and stirred at room temperature for 16 hours. The reaction mixture was poured into water (500 mL) and the formed precipitate was filtered off. The filter cake was washed with water (1 L) and dried to give tert-butyl N-[(1S)-2-[methoxy(methyl)amino]-1-methyl-2-oxo-ethyl]carbamate (36 g) as a white powder. tert-butyl N-[(1S)-2-[methoxy(methyl)amino]-1-methyl-2-oxo-ethyl]carbamate (35 g, 151 mmol) was dissolved in THF (500 mL) and cooled to 0° C. Methylmagnesium bromide (3.0 M in diethyl ether, 140 mL) was added and the reaction mixture was stirred 16 hours at room temperature. The reaction mixture was poured into water (100 mL) and evaporated to dryness. The residue was dissolved in EtOAc, washed with water, dried over Na$_2$SO$_4$, filtered and evaporated to dryness yielding tert-butyl N-[(1S)-1-methyl-2-oxo-propyl]carbamate (22 g) as a white powder. To a cooled (−78° C.) solution of tert-butyl N-[(1S)-1-methyl-2-oxo-propyl]carbamate (12 g, 64.1 mmol) in CH$_2$Cl$_2$ (200 mL) bis(2-methoxyethyl)-aminosulfur trifluoride (18.9 g, 117.5 mmol) was added. The reaction mixture was allowed to warm to room temperature and stirred overnight. The reaction mixture was poured into water and extracted with CH$_2$Cl$_2$. The organic layer was washed with water, dried over Na$_2$SO$_4$, filtered and evaporated to dryness. The obtained residue was purified by silica gel chromatography yielding tert-butyl N-[(1S)-2,2-difluoro-1-methyl-propyl]carbamate (5.8 g) as a pale yellow solid. Tert-butyl N-[(1S)-2,2-difluoro-1-methyl-propyl]carbamate (5.8 g, 27.7 mmol) was dissolved in EtOAc (100 mL). HCl (g) was bubbled through for 30 minutes and then the volatiles were removed under reduced pressure yielding (2S)-3,3-difluorobutan-2-amine hydrochloride (3.8 g)$^1$H NMR (400 MHz, DMSO-d$_6$) δ ppm 8.69 (br. s., 3H), 3.76-3.63 (m, 1H), 1.72 (t, J=19.7 Hz, 3H), 1.28 (d, J=6.8 Hz, 3H).

Compound 47: 5-[[(1S)-2,2-difluoro-1-methyl-propyl]sulfamoyl]-N-(3,4-difluorophenyl)-2-methyl-thiophene-3-carboxamide

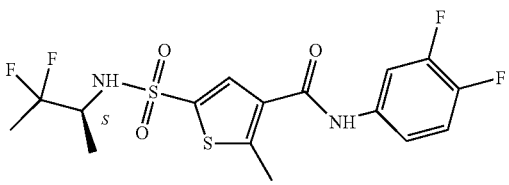

To a solution of (S)-3,3-difluorobutan-2-amine hydrochloride (116.5 mg, 0.8 mmol) and triethylamine (304 mg, 3 mmol) in CH$_2$Cl$_2$ (4 mL) was added drop wise a solution of 4-[(3,4-difluorophenyl)carbamoyl]-5-methyl-thiophene-2-sulfonyl chloride (250 mg, 0.71 mmol) in CH$_2$Cl$_2$ (4 mL). The reaction mixture was stirred for 12 hours at room temperature. The volatiles were removed under reduced pressure and the residue was purified by high performance liquid chromatography to give compound 47 (206 mg). Method F; Rt: 4.37 min. m/z: 425.0 (M+H)$^+$ Exact mass: 424.1. $^1$H NMR (400 MHz, DMSO-d$_6$) δ ppm 10.35 (br. s, 1H), 8.40 (br. s., 1H), 8.04 (s, 1H), 7.92-7.86 (m, 1H), 7.52-7.37 (m, 2H), 3.68-3.52 (s., 1H), 2.72 (s, 3H), 1.59 (t, J=19.2 Hz, 3H), 0.98 (d, J=6.8 Hz, 3H).

Synthesis of 4-[(3-bromo-4-fluoro-phenyl)carbamoyl]-5-methyl-thiophene-2-sulfonyl chloride 5-chlorosulfonyl-2-methyl-thiophene-3-carbonyl chloride (1.66 g, 6.41 mmol) was dissolved in toluene (75 mL) and brought to reflux. 3-bromo-4-fluoroaniline (1.2 g, 6.41 mmol) was added portion wise in 2 minutes. After addition the reaction was refluxed for 2 hours. The reaction mixture was allowed to reach room temperature and the formed precipitate was filtered off yielding 4-[(3-bromo-4-fluoro-phenyl)carbamoyl]-5-methyl-thiophene-2-sulfonyl chloride as a brown powder (1.39 g).

Compound 48: N-(3-bromo-4-fluoro-phenyl)-2-methyl-5-[[(1R)-2,2,2-trifluoro-1-methyl-ethyl]sulfamoyl]thiophene-3-carboxamide

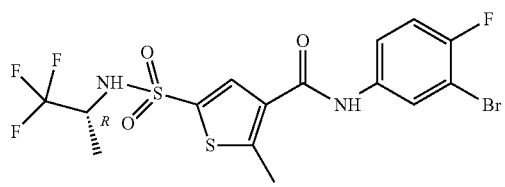

Compound 48 (99.8 mg) was prepared similarly as described for compound 36, starting from 4-[(3-bromo-4-fluoro-phenyl)carbamoyl]-5-methyl-thiophene-2-sulfonyl chloride (250 mg, 0.61 mmol) instead of 4-[(3-chloro-4,5-difluoro-phenyl)carbamoyl]-5-methyl-thiophene-2-sulfonyl chloride and stirring overnight at 80° C. Method A; Rt: 2.06 min. m/z: 489 (M+H)$^+$ Exact mass: 488.0. $^1$H NMR (400

MHz, DMSO-$d_6$) δ ppm 1.09 (d, J=6.8 Hz, 3H), 2.72 (s, 3H), 4.00-4.14 (m, 1H), 7.38 (t, J=8.8 Hz, 1H), 7.70 (ddd, J=9.0, 4.4, 2.6 Hz, 1H), 8.07 (s, 1H), 8.13 (dd, J=6.4, 2.4 Hz, 1H), 8.83 (d, J=8.6 Hz, 1H), 10.30 (s, 1H).

Compound 49: N-(3,4-difluorophenyl)-2-methyl-5-[[3-(trifluoromethyl)tetrahydrofuran-3-yl]sulfamoyl]thiophene-3-carboxamide

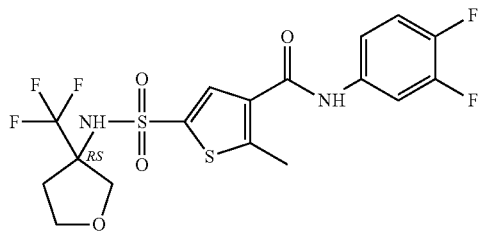 [SMILES: Cc1sc(S(=O)(=O)NC2(C(F)(F)F)CCOC2)cc1C(=O)Nc1ccc(F)c(F)c1]

Compound 49 (26.4 mg) was prepared similarly as described for compound 41, using 800 mg of 4-[(3,4-difluorophenyl)carbamoyl]-5-methyl-thiophene-2-sulfonyl chloride instead of 5-methyl-4-[[3-(trifluoromethyl)phenyl]carbamoyl]thiophene-2-sulfonyl chloride and 3-(trifluoromethyl)tetrahydrofuran-3-amine (460 mg). Purification by high performance liquid chromatography (Column: Gemini C18 150*25 mm*10 ul. A: base water B: MeCN. Flow Rate (mL/min): 25). Method E; Rt: 5.65 min. m/z: 471.2 (M+H)$^+$ Exact mass: 470.0. $^1$H NMR (400 MHz, DMSO-$d_6$) δ ppm 10.35 (s, 1H), 9.14 (br. s., 1H), 8.01 (s, 1H), 7.88 (m, J=2.3, 7.6, 13.2 Hz, 1H), 7.50-7.38 (m, 2H), 4.09 (d, J=10.5 Hz, 1H), 3.95 (d, J=10.5 Hz, 1H), 3.85 (m, J=4.5, 8.5 Hz, 1H), 3.60 (m, J=7.8 Hz, 1H), 2.72 (s, 3H), 2.45 (m, J=7.0 Hz, 1H), 2.25 (m, J=8.1, 13.9 Hz, 1H).

Compound 50: N-(3,4-difluorophenyl)-2-methyl-5-[(2,2,2-trifluoro-1,1-dimethyl-ethyl)sulfamoyl]thiophene-3-carboxamide

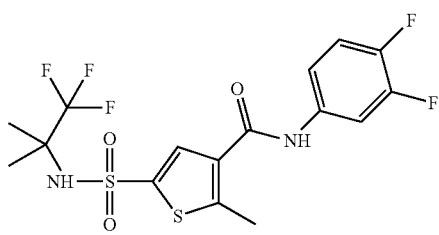 [SMILES: Cc1sc(S(=O)(=O)NC(C)(C)C(F)(F)F)cc1C(=O)Nc1ccc(F)c(F)c1]

Compound 50 (62.9 mg) was prepared similarly as described for compound 42, using 4-[(3,4-difluorophenyl)carbamoyl]-5-methyl-thiophene-2-sulfonyl chloride (250 mg, 0.71 mmol) instead of 5-methyl-4-[[3-(trifluoromethyl)phenyl]carbamoyl]thiophene-2-sulfonyl chloride and 2,2,2-trifluoro-1,1-dimethyl-ethylamine (100 mg, 0.79 mmol). Method E; Rt: 5.92 min. m/z: 443.2 (M+H)$^+$ Exact mass: 442.0. $^1$H NMR (400 MHz, DMSO-$d_6$) δ ppm 10.35 (s, 1H), 8.75 (br. s., 1H), 8.01 (s, 1H), 7.89 (ddd, J=2.5, 7.5, 13.3 Hz, 1H), 7.52-7.33 (m, 2H), 2.76-2.66 (m, 3H), 1.38 (s, 6H).

Compound 51: N-(3-cyano-4-fluoro-phenyl)-2-methyl-5-[[(1R)-2,2,2-trifluoro-1-methyl-ethyl]sulfamoyl]thiophene-3-carboxamide

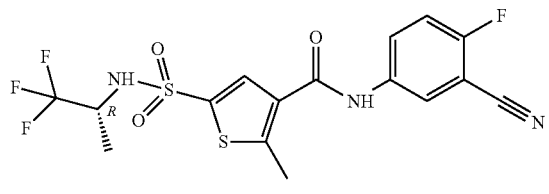

Compound 51 (527.5 mg) was prepared similarly as described for compound 36, starting from 4-[(3-cyano-4-fluoro-phenyl)carbamoyl]-5-methyl-thiophene-2-sulfonyl chloride (500 mg, 1.39 mmol) and using (R)-1,1,1-trifluoro-2-propylamine (473 mg, 4.18 mmol). Method B; Rt: 1.03 min. m/z: 434 (M−H)$^-$ Exact mass: 435.0. $^1$H NMR (400 MHz, DMSO-$d_6$) δ ppm 1.10 (d, J=7.0 Hz, 3H), 2.74 (s, 3H), 4.07 (dq, J=14.8, 7.4 Hz, 1H), 7.55 (t, J=9.1 Hz, 1H), 8.01 (ddd, J=9.2, 5.0, 2.8 Hz, 1H), 8.08 (s, 1H), 8.22 (dd, J=5.8, 2.8 Hz, 1H), 8.86 (d, J=8.4 Hz, 1H), 10.46 (s, 1H).

Compound 52: N-(3,4-difluorophenyl)-5-[[2-fluoro-1-(fluoromethyl)ethyl]sulfamoyl]-2-meth thiophene-3-carboxamide

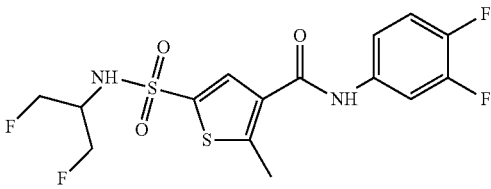 [SMILES: Cc1sc(S(=O)(=O)NC(CF)CF)cc1C(=O)Nc1ccc(F)c(F)c1]

4-[(3,4-difluorophenyl)carbamoyl]-5-methyl-thiophene-2-sulfonyl chloride (300 mg, 0.85 mmol) was dissolved in CH$_2$Cl$_2$ (10 mL). 1,3-difluoro-2-propylamine hydrochloride (124 mg, 0.94 mmol) and triethylamine (214 mg, 2.11 mmol) were added and the mixture was stirred at room temperature for 2 hours. The reaction mixture was poured into water, and the separated organic layer was washed with water, dried over Na$_2$SO$_4$ and evaporated to dryness to provide an oil. The residue was purified by preparative high performance liquid chromatography over RP-18 (eluent: CH$_3$CN in H$_2$O (0.1% FA) from 20% to 60%, v/v). The pure fractions were collected and evaporated to dryness to provide compound 52 (97.1 mg) as a white solid. Method E; Rt: 5.38 min. m/z: 411.1 (M+H)$^+$ Exact mass: 410.0. $^1$H NMR (400 MHz, DMSO-$d_6$) δ ppm 10.35 (s, 1H), 8.67 (br. s, 1H), 8.03 (s, 1H), 7.91-7.86 (m, 1H), 7.52-7.36 (m, 2H), 4.48 (d, J=4.5 Hz, 2H), 4.36 (d, J=4.5 Hz, 2H), 3.84-3.69 (m, 1H), 2.71 (s, 3H).

Compound 53: N-(3-cyano-4-fluoro-phenyl)-2-methyl-5-[[1-(trifluoromethyl)cyclo-propyl]sulfamoyl]thiophene-3-carboxamide

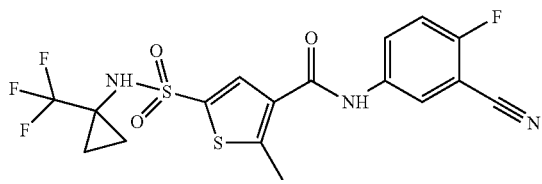 [SMILES: Cc1sc(S(=O)(=O)NC2(C(F)(F)F)CC2)cc1C(=O)Nc1ccc(F)c(C#N)c1]

Compound 53 (39.6 mg) was prepared similarly as described for compound 36, starting from 4-[(3-cyano-4-fluoro-phenyl)carbamoyl]-5-methyl-thiophene-2-sulfonyl chloride (100 mg, 0.28 mmol) and 1-trifluoromethyl-1-cyclopropylamine (105 mg, 0.84 mmol) and additional heating for 16 hours at 100° C. Method A; Rt: 1.90 min. m/z: 448 (M+H)$^+$ Exact mass: 447.0. $^1$H NMR (400 MHz, DMSO-d$_6$) δ ppm 1.12-1.18 (m, 2H), 1.21-1.29 (m, 2H), 2.72 (s, 3H), 7.55 (t, J=9.1 Hz, 1H), 7.97-8.04 (m, 2H), 8.22 (dd, J=5.9, 2.6 Hz, 1H), 9.42 (s, 1H), 10.46 (s, 1H).

Compound 54: N-(3-cyano-4-fluoro-phenyl)-2-methyl-5-[[3-(trifluoromethyl)tetrahydrofuran-3-yl]sulfamoyl]thiophene-3-carboxamide

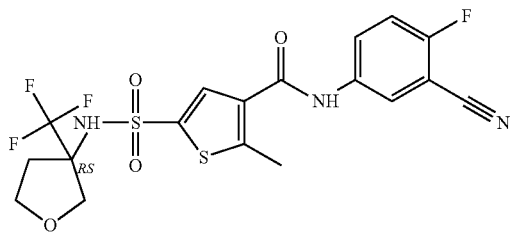 [SMILES: Cc1sc(S(=O)(=O)NC2(C(F)(F)F)CCOC2)cc1C(=O)Nc1ccc(F)c(C#N)c1]

Compound 54 (racemic, 46.5 mg) was prepared similarly as described for compound 41, using 4-[(3-cyano-4-fluoro-phenyl)carbamoyl]-5-methyl-thiophene-2-sulfonyl chloride (800 mg, 2.23 mmol) and 3-(trifluoromethyl)tetrahydrofuran-3-amine (460 mg). Purification by high performance liquid chromatography (Column: YMC-pack ODS-AQ 150*20 mm*5 um. A: base water B: MeCN. Flow Rate (mL/min): 25). Method G; Rt: 4.52 min. m/z: 495.0 (M+NH$_4$)$^+$ Exact mass: 477.0. $^1$H NMR (400 MHz, DMSO-d$_6$) δ ppm 10.47 (s, 1H), 9.15 (br. s., 1H), 8.22 (dd, J=2.5, 5.8 Hz, 1H), 8.07-7.97 (m, 2H), 7.55 (m, J=9.2 Hz, 1H), 4.09 (d, J=10.3 Hz, 1H), 3.95 (d, J=10.3 Hz, 1H), 3.85 (m, J=4.5, 8.3 Hz, 1H), 3.61 (m, J=7.5 Hz, 1H), 2.73 (s, 3H), 2.47-2.43 (m, 1H), 2.29-2.19 (m, 1H).

Synthesis of (2R)-3,3-difluorobutan-2-amine (R)-2-((tert-butoxycarbonyl)amino)propanoic acid (30 g, 159 mmol), N,O-dimethyl-hydroxylamine hydrochloride (17.5 g, 178 mmol), HATU (74 g, 195 mmol) and N,N-diisopropylethylamine (30 g, 232 mmol) were dissolved in DMF (300 mL) and stirred at room temperature for 15 hours. The reaction mixture was concentrated under vacuum and the residue was dissolved in CH$_2$Cl$_2$ (500 mL) and washed with brine (3×200 mL). The organic layer was dried over Na$_2$SO$_4$ and concentrated in vacuo. The residue was purified via silica gel chromatography using petroleum ether:EtOAc 2:1 as eluent yielding tert-butyl N-[(1R)-2-[methoxy(methyl)amino]-1-methyl-2-oxo-ethyl]carbamate (28.9 g). tert-butyl N-[(1R)-2-[methoxy(methyl)amino]-1-methyl-2-oxo-ethyl]carbamate was dissolved in THF (300 mL) and cooled to 0° C. Methylmagnesium bromide 3.0 m in diethyl ether (85 mL, 255 mmol) was added drop wise and the reaction mixture was stirred 15 hours at room temperature. The reaction mixture was quenched with sat. NH$_4$Cl and extracted with CH$_2$Cl$_2$ (3×100 mL). The combined organic layers were dried over Na$_2$SO$_4$, filtered and evaporated to dryness. The obtained residue was purified via silica gel chromatography yielding tert-butyl N-[(1R)-1-methyl-2-oxo-propyl]carbamate (18.9 g). To a cooled (−78° C.) solution of tert-butyl N-[(1R)-1-methyl-2-oxo-propyl]carbamate (10 g, 53.4 mmol) in CH$_2$Cl$_2$ (200-mL) bis(2-methoxyethyl)aminosulfur trifluoride (18.9 g, 117.5 mmol) was added drop wise and stirring was continued for 2 hours at −78° C. The reaction mixture was allowed to warm to room temperature and stirred overnight. The reaction mixture was quenched with sat. NaHCO$_3$ and extracted with EtOAc. The combined organic layers were washed with brine, dried over MgSO$_4$, filtered and evaporated to dryness.

The residue was purified by silica gel chromatography using a gradient from petroleum ether to petroleum ether:EtOAc 1:1 yielding tert-butyl N-[(1R)-2,2-difluoro-1-methyl-propyl]carbamate (6.77 g). Tert-butyl N-[(1R)-2,2-difluoro-1-methyl-propyl]carbamate (6.77 g) was dissolved in EtOAc (50 mL). HCl in EtOAc was added at 0° C. and the reaction mixture was stirred for 4 hours at room temperature. The formed precipitate was filtered off and dried under high vacuum yielding (2R)-3,3-difluorobutan-2-amine hydrochloride (3.5 g).

Compound 55: 5-[[(1R)-2,2-difluoro-1-methyl-propyl]sulfamoyl]-N-(3,4-difluorophenyl)-2-methyl-thiophene-3-carboxamide

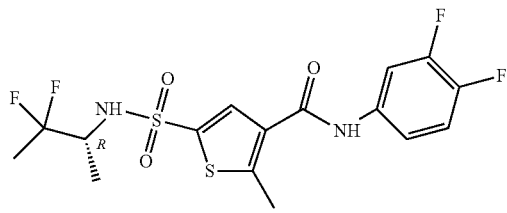

Compound 55 (186 mg) was prepared similarly as described for compound 47 using (2R)-3,3-difluorobutan-2-amine hydrochloride instead of (2S)-3,3-difluorobutan-2-amine hydrochloride and DIPEA instead of NEt$_3$. The crude compound was purified by high-performance liquid chromatography (Column: ADIKMA Diamonsil(2) C18, 150*25*5 um, Flow rate: 35 mL/min, Mobile Phase A: Purified water (containing 0.5% HCl), Mobile Phase B: CH$_3$CN, Gradient: 53-83% (% B) and Supercritical Fluid Chromatography (Column: AD-250 ~30 mm, Flow rate: 60 mL/min, Mobile Phase A: CO$_2$/EtOH (0.1% NH$_3$.H$_2$O) 30%). $^1$H NMR (400 MHz, DMSO-d$_6$) δ: 10.34 (br. s, 1H), 8.44 (br. s., 1H), 8.03 (s, 1H), 7.92-7.82 (m, 1H), 7.52-7.37 (m, 2H), 3.68-3.52 (m., 1H), 2.72 (s, 3H), 1.59 (t, J=19.0 Hz, 3H), 0.98 (d, J=6.8 Hz, 3H).

Method H; Rt: 5.23 min. m/z: 425.0 (M+H)$^+$ Exact mass: 424.1.

Compound 56: N-(3,4-difluorophenyl)-2-methyl-5-[[(1R)-2,2,2-trifluoro-1-methyl-ethyl]sulfamoyl]thiophene-3-carboxamide

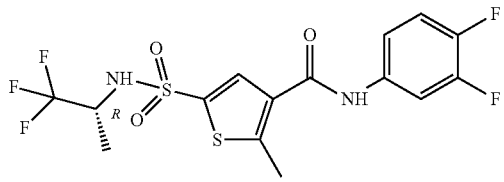

Compound 56 (39.6 mg) was prepared similarly as described for compound 36, starting from 4-[(3,4-difluorophenyl)carbamoyl]-5-methyl-thiophene-2-sulfonyl chloride (130 mg, 0.37 mmol) instead of 4-[(3-chloro-4,5-difluorophenyl)carbamoyl]-5-methylthiophene-2-sulfonyl chloride and (R)-1,1,1-trifluoro-2-propylamine (125 mg, 1.11 mmol). Method B; Rt: 1.08 min. m/z: 427 (M–H)⁻ Exact mass: 428.0. ¹H NMR (400 MHz, DMSO-d₆) δ ppm 1.09 (d, J=6.8 Hz, 3H), 2.72 (s, 3H), 4.02-4.13 (m, 1H), 7.38-7.51 (m, 2H), 7.88 (ddd, J=13.3, 7.5, 2.3 Hz, 1H), 8.06 (s, 1H), 8.83 (br. s., 1H), 10.34 (s, 1H).

Biological Examples

Anti-HBV Activity of Compounds of Formula (I)

The anti-HBV activity was measured using a stable transfected cell line, HepG2.2.15. This cell line was described to secrete relatively consistent high levels of HBV virion particles, which have been shown to cause both acute and chronic infection and disease in chimpanzees.

For the antiviral, assay cells were treated twice for three days with serially diluted compound in 96-well plates in duplicate. After 6 days of treatment the antiviral activity was determined by quantification of purified HBV DNA from secreted virions using realtime PCR and an HBV specific primer set and probe.

The anti HBV activity was also measured using the HepG2.117 cell line, a stable, inducibly HBV producing cell line, which replicates HBV in the absence of doxicycline (Tet-off system). For the antiviral assay, HBV replication was induced, followed by a treatment with serially diluted compound in 96-well plates in duplicate. After 3 days of treatment, the antiviral activity was determined by quantification of intracellular HBV DNA using realtime PCR and an HBV specific primer set and probe.

Cytotoxicity of the compounds was tested using HepG2 cells, incubated for 4 days in the presence of compounds. The viability of the cells was assessed using a Resazurin assay. Results are displayed in Table 1.

TABLE 1

| Co. No. | HepG2 2.15 EC50 (µM) | HepG2 117 EC50 (µM) | HepG2 4 days CC50 (µM) |
|---|---|---|---|
| 1 | 0.17 | 0.32 | >25 |
| 2 | 0.81 | 1.9 | >25 |
| 3 | 0.21 | 0.34 | >25 |
| 4 | 0.57 | 0.56 | >25 |
| 5 | 1.67 | 1.18 | >25 |
| 6 | 0.58 | 0.68 | >25 |
| 7 | 0.17 | 0.16 | >25 |
| 8 | 0.10 | 0.16 | >25 |
| 9 | 0.79 | 1.1 | >25 |
| 10 | 0.43 | 0.56 | >25 |
| 11 | 0.19 | 0.31 | >25 |
| 12 | 0.16 | 0.19 | >25 |
| 13 | 1.7 | 0.94 | >25 |
| 14 | 0.63 | 0.13 | >25 |
| 15 | 0.027 | 0.16 | >25 |
| 16 | 0.054 | 0.048 | >25 |
| 16a | 0.075 | 0.087 | >25 |
| 16b | 0.028 | 0.026 | >25 |
| 17 | 0.12 | 0.13 | 11.7 |
| 18 | 0.065 | 0.082 | 14.6 |
| 19 | 0.063 | 0.10 | >25 |
| 20 | 0.17 | 0.11 | 15.9 |
| 21 | 0.32 | >1 | 10.5 |
| 22 | 0.25 | 0.23 | >25 |
| 23 | 0.11 | 0.032 | 18.1 |
| 24 | 0.12 | 0.15 | >25 |
| 25 | 0.053 | 0.058 | >25 |
| 26 | 0.17 | 0.051 | 11.5 |
| 27 | 0.13 | 0.090 | 12.2 |
| 28 | 0.034 | 0.041 | >25 |
| 29 | 0.12 | 0.12 | 13.2 |
| 30 | >1 | 0.79 | >25 |
| 31 | 0.52 | 0.17 | >25 |
| 32 | 0.22 | 0.30 | >25 |
| 33 | 0.14 | 0.13 | >25 |
| 34 | 0.10 | 0.13 | 17.7 |
| 35 | 0.06 | 0.04 | >25 |
| 36 | 0.14 | 0.16 | 7.1 |
| 37 | 0.16 | 0.22 | 8.2 |
| 38 | 0.04 | 0.08 | 14.4 |
| 39 | 0.07 | 0.06 | >25 |
| 40 |  | 0.50 | >25 |
| 41 | 0.55 | >1 | >25 |
| 42 | 0.53 | >1 | 16.9 |
| 43 | 0.33 | 0.67 | >25 |
| 44 | 0.82 | 0.45 | >25 |
| 45 | 0.28 | 0.42 | >25 |
| 46 | 0.40 | 0.42 | >25 |
| 47 | 0.16 | 0.34 | 14.3 |
| 48 | 0.16 | 0.28 | 7.73 |
| 49 | 0.29 | 0.27 | >25 |
| 50 | 0.14 | 0.19 | >25 |
| 51 | 0.25 | 0.17 | >25 |
| 52 | 0.17 | 0.17 | >25 |
| 53 | 0.12 | 0.14 | 13.7 |
| 54 | 0.18 | 0.10 | >25 |
| 55 | 0.032 | 0.09 | 14.6 |
| 56 | 0.13 | 0.07 | 14.9 |

The invention claimed is:
1. A compound of Formula (I)

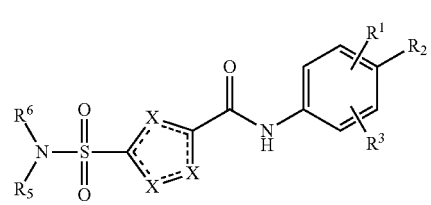

or a stereoisomer or tautomeric form thereof, wherein:
X is S or CR⁴, wherein one X is S and the other two X are each CR⁴;
R² is fluoro or hydrogen;

R¹ and R³ are each independently selected from the group consisting of hydrogen, fluoro, chloro, bromo, $CHF_2$, $CH_2F$, $CF_3$, CN and methyl, wherein, if R² is hydrogen, at least one of R¹ and R³ is selected from the group consisting of fluoro, chloro, bromo, $CHF_2$, $CH_2F$, $CF_3$, CN;

R⁴ is selected from the group consisting of hydrogen, halogen, $C_1$-$C_3$alkyl, cyclopropyl, $CHF_2$, $CH_2F$ and $CF_3$, wherein at least one R⁴ is hydrogen;

R⁵ is hydrogen;

R⁶ is selected from the group consisting of $C_1$-$C_6$alkyl, $C_1$-$C_3$alkyl-R⁷, and a 3-7 membered saturated ring optionally containing one or more heteroatoms, each heteroatom independently selected from the group consisting of O, S and N, wherein each of said 3-7 membered saturated ring and $C_1$-$C_6$alkyl is independently optionally substituted with one or more substituents, each substituent independently selected from the group consisting of hydrogen, fluoro, OH, $CF_3$ and $C_1$-$C_4$alkyl;

R⁷ is a 3-7 membered saturated ring optionally containing one or more heteroatoms, each heteroatom independently selected from the group consisting of O, S and N, and wherein said 3-7 membered saturated ring is optionally substituted with C(=O)—R⁸;

R⁸ is selected from the group consisting of $C_1$-$C_3$alkoxy and —$NH_2$;

wherein if R¹ is methyl, R² is fluoro, and R³ is hydrogen, then R⁶ is not methyl;

or a pharmaceutically acceptable salt or a solvate thereof.

2. The compound according to claim 1, wherein R¹ is fluoro or methyl.

3. The compound according to claim 1 having a Formula (II)

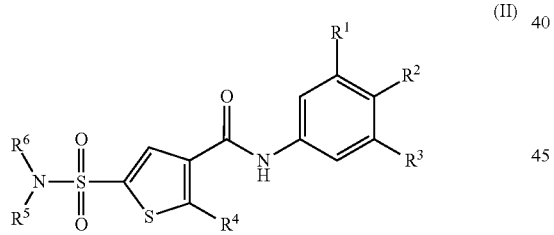

wherein R⁴ is selected from the group consisting of hydrogen, halogen, $C_1$-$C_3$alkyl, cyclopropyl, $CHF_2$, $CH_2F$ and $CF_3$.

4. The compound according to claim 1 wherein at least two of R¹, R² and R³ are each halogen.

5. The compound according to claim 1 wherein R¹ is methyl and R² is fluoro.

6. The compound according to claim 1 wherein R⁶ is a 3-7 membered saturated ring optionally containing one oxygen.

7. The compound according to claim 1 wherein R⁶ is a 4 or 5 membered saturated ring containing one oxygen.

8. The compound according to claim 1 wherein R⁶ is a branched $C_1$-$C_6$alkyl optionally substituted with one or more fluoro.

9. A method of treating HBV infection in a subject comprising administering to said subject a therapeutically effective amount of at least one compound according to claim 1.

10. A pharmaceutical composition comprising a compound according to claim 1, and a pharmaceutically acceptable carrier.

11. A product containing (a) a compound according to claim 1, and (b) at least one HBV inhibitor, as a combined preparation for simultaneous, separate or sequential use in the treatment of HBV infection.

12. The compound according to claim 1 selected from the group consisting of:

N-(4-fluoro-3-methyl-phenyl)-5-[[(3S)-tetrahydrofuran-3-yl]sulfamoyl]thiophene-3-carboxamide;

2-bromo-N-(4-fluoro-3-methyl-phenyl)-5-[[(3S)-tetrahydrofuran-3-yl]-sulfamoyl]thiophene-3-carboxamide;

2-chloro-N-(4-fluoro-3-methyl-phenyl)-5-[[(1R)-2-hydroxy-1-methyl-ethyl]sulfamoyl]thiophene-3-carboxamide;

2-chloro-N-(4-fluoro-3-methyl-phenyl)-5-[[(3S)-tetrahydrofuran-3-yl]-sulfamoyl]thiophene-3-carboxamide;

N-(4-fluoro-3-methyl-phenyl)-5-[[(3S)-tetrahydrofuran-3-yl]sulfamoyl]-2-(trifluoromethyl)thiophene-3-carboxamide;

2-cyclopropyl-N-(4-fluoro-3-methyl-phenyl)-5-[[(3S)-tetrahydrofuran-3-yl]sulfamoyl]thiophene-3-carboxamide;

N-(4-fluoro-3-methyl-phenyl)-2-methyl-5-[[(3S)-tetrahydrofuran-3-yl]-sulfamoyl]thiophene-3-carboxamide;

N-(4-fluoro-3-methyl-phenyl)-4-[[(3S)-tetrahydrofuran-3-yl]sulfamoyl]thiophene-2-carboxamide;

N-(4-fluoro-3-methyl-phenyl)-5-methyl-4-[[(3S)-tetrahydrofuran-3-yl]-sulfamoyl]thiophene-2-carboxamide;

N-(4-fluoro-3-methyl-phenyl)-5-methyl-4-[(3-methyloxetan-3-yl)sulfamoyl]thiophene-2-carboxamide;

N-(4-fluoro-3-methyl-phenyl)-3-methyl-4-[[(3S)-tetrahydrofuran-3-yl]-sulfamoyl]thiophene-2-carboxamide;

N-(4-fluoro-3-methyl-phenyl)-3-methyl-4-[(3-methyloxetan-3-yl)sulfamoyl]thiophene-2-carboxamide;

N-(4-fluoro-3-methyl-phenyl)-5-[[(3S)-tetrahydrofuran-3-yl]sulfamoyl]thiophene-2-carboxamide;

2-ethyl-N-(4-fluoro-3-methyl-phenyl)-5-[[(3S)-tetrahydrofuran-3-yl]-sulfamoyl]thiophene-3-carboxamide;

N-(4-fluoro-3-methyl-phenyl)-2-methyl-5-[(3-methyloxetan-3-yl)sulfamoyl]thiophene-3-carboxamide;

N-(4-fluoro-3-methyl-phenyl)-2-methyl-5-[(3-methyltetrahydrofuran-3-yl)sulfamoyl]thiophene-3-carboxamide;

5-(tert-butylsulfamoyl)-N-(3,4-difluorophenyl)-2-methyl-thiophene-3-carboxamide;

N-(3,4-difluorophenyl)-2-methyl-5-[[(1R)-1-methylpropyl]sulfamoyl]thiophene-3-carboxamide;

N-(3-chloro-4,5-difluoro-phenyl)-2-methyl-5-[(3-methyloxetan-3-yl)-sulfamoyl]thiophene-3-carboxamide;

5-(tert-Butylsulfamoyl)-N-(3-chloro-4,5-difluorophenyl)-2-methylthiophene-3-carboxamide;

5-(tert-butyl sulfamoyl)-2-methyl-N-[3-(trifluoromethyl)phenyl]thiophene-3-carboxamide;

2-methyl-5-[(3-methyloxetan-3-yl)sulfamoyl]-N-[3-(trifluoromethyl)phenyl]thiophene-3-carboxamide;

5-(tert-Butylsulfamoyl)-N-(3,4-difluoro-5-methylphenyl)-2-methylthiophene-3-carboxamide;

5-(tert-Butylsulfamoyl)-N-(3-cyano-4-fluorophenyl)-2-methylthiophene-3-carboxamide;

5-(tert-Butylsulfamoyl)-N-(4-fluoro-3-methylphenyl)-2-methylthiophene-3-carboxamide;

5-(tert-Butylsulfamoyl)-N-(3-chloro-4-fluorophenyl)-2-methylthiophene-3-carboxamide;

N-(3-Bromo-4-fluorophenyl)-5-(tert-butylsulfamoyl)-2-methylthiophene-3-carboxamide;

N-(3-Chloro-4-fluorophenyl)-2-methyl-5-[(3-methyloxetan-3-yl)sulfamoyl]thiophene-3-carboxamide;

N-(3-Bromo-4-fluorophenyl)-2-methyl-5-[(3-methyloxetan-3-yl)sulfamoyl]thiophene-3-carboxamide;

methyl N-({4-[(3,4-difluorophenyl)carbamoyl]-5-methylthiophen-2-yl}sulfonyl)-2-methylalaninate;

methyl N-({4-[(4-fluoro-3-methylphenyl)carbamoyl]-5-methylthiophen-2-yl}sulfonyl)-2-methylalaninate;

5-[(2-amino-1,1-dimethyl-2-oxoethyl)sulfamoyl]-N-(3,4-difluorophenyl)-2-methylthiophene-3-carboxamide;

5-[(2-amino-1,1-dimethyl-2-oxoethyl)sulfamoyl]-N-(4-fluoro-3-methylphenyl)-2-methylthiophene-3-carboxamide;

N-(3,4-difluorophenyl)-2-methyl-5-{[1-(trifluoromethyl)cyclopropyl]-sulfamoyl}thiophene-3-carboxamide;

N-(4-fluoro-3-methylphenyl)-2-methyl-5-{[1-(trifluoromethyl)cyclo-propyl]sulfamoyl}thiophene-3-carboxamide;

N-(3-chloro-4,5-difluorophenyl)-2-methyl-5-{[(1R)-2,2,2-trifluoro-1-methylethyl]sulfamoyl}thiophene-3-carboxamide;

N-(3-chloro-4,5-difluorophenyl)-2-methyl-5-{[(1 S)-2,2,2-trifluoro-1-methylethyl]sulfamoyl}thiophene-3-carboxamide;

N-(3-chloro-4-fluorophenyl)-2-methyl-5-{[(1R)-2,2,2-trifluoro-1-methylethyl]sulfamoyl}thiophene-3-carboxamide;

N-(4-fluoro-3-methylphenyl)-2-methyl-5-{[(1R)-2,2,2-trifluoro-1-methylethyl]sulfamoyl}thiophene-3-carboxamide;

N-(3-chloro-4, 5-difluoro-phenyl)-2-methyl-5-[(2,2,2-trifluoro-1,1-dimethyl-ethyl)sulfamoyl]thiophene-3-carboxamide;

2-methyl-N-[3-(trifluoromethyl)phenyl]-5-[[3-(trifluoromethyl)tetrahydrofuran-3-yl]sulfamoyl]thiophene-3-carboxamide;

2-methyl-5-[(2,2,2-trifluoro-1,1-dimethyl-ethyl)sulfamoyl]-N-[3-(trifluoromethyl)phenyl]thiophene-3-carboxamide;

N-(3-cyano-4-fluoro-phenyl)-5-[[2-fluoro-1-(fluoromethyl)ethyl]sulfamoyl]-2-methyl-thiophene-3-carboxamide;

N-(3-cyano-4-fluoro-5-methyl-phenyl)-2-methyl-5-[(3-methyloxetan-3-yl)sulfamoyl]thiophene-3-carboxamide;

N-(3-cyano-4-fluoro-phenyl)-2-methyl-5-[(2,2,2-trifluoro-1,1-dimethyl-ethyl)sulfamoyl]thiophene-3-carboxamide;

N-(3-cyano-4-fluoro-phenyl)-2-methyl-5-[[(1S)-2,2,2-trifluoro-1-methyl-ethyl]sulfamoyl]thiophene-3-carboxamide;

5-[[(1S)-2,2-difluoro-1-methyl-propyl]sulfamoyl]-N-(3,4-difluorophenyl)-2-methyl-thiophene-3-carboxamide;

N-(3-bromo-4-fluoro-phenyl)-2-methyl-5-[[(1R)-2,2,2-trifluoro-1-methyl-ethyl]sulfamoyl]thiophene-3-carboxamide;

N-(3,4-difluorophenyl)-2-methyl-5-[[3-(trifluoromethyl)tetrahydrofuran-3-yl]sulfamoyl]thiophene-3-carboxamide;

N-(3,4-difluorophenyl)-2-methyl-5-[(2,2,2-trifluoro-1,1-dimethyl-ethyl)sulfamoyl]thiophene-3-carboxamide;

N-(3-cyano-4-fluoro-phenyl)-2-methyl-5-[[(1R)-2,2,2-trifluoro-1-methyl-ethyl]sulfamoyl]thiophene-3-carboxamide;

N-(3,4-difluorophenyl)-5-[[2-fluoro-1-(fluoromethyl)ethyl]sulfamoyl]-2-methyl-thiophene-3-carboxamide;

N-(3-cyano-4-fluoro-phenyl)-2-methyl-5-[[1-(trifluoromethyl)cyclo-propyl]sulfamoyl]thiophene-3-carboxamide;

N-(3-cyano-4-fluoro-phenyl)-2-methyl-5-[[3-(trifluoromethyl)tetrahydrofuran-3-yl]sulfamoyl]thiophene-3-carboxamide;

5-[[(1R)-2,2-difluoro-1-methyl-propyl]sulfamoyl]-N-(3,4-difluorophenyl)-2-methyl-thiophene-3-carboxamide; and N-(3,4-difluorophenyl)-2-methyl-5-[[(1R)-2,2,2-trifluoro-1-methyl-ethyl]sulfamoyl]thiophene-3-carboxamide.

13. A pharmaceutical composition comprising a compound according to claim 12, and a pharmaceutically acceptable carrier.

14. A method of treating HBV infection in a subject comprising administering to said subject a therapeutically effective amount of at least one compound according to claim 12.

15. The compound according to claim 1, wherein
$R^1$ and $R^3$ are each independently selected from the group consisting of hydrogen, chloro, bromo, $CF_3$, CN and methyl;
$R^2$ is fluoro;
$R^4$ is selected from the group consisting of hydrogen and methyl; and
$R^6$ is a 3-7 membered saturated ring containing one O heteroatom, wherein said 3-7 membered saturated ring is substituted with a substituent selected from the group consisting of hydrogen, $CF_3$ and methyl.

16. The compound according to claim 1, wherein
$R^1$ and $R^3$ are each independently selected from the group consisting of $CF_3$ and CN;
$R^2$ is hydrogen;
$R^4$ is selected from the group consisting of hydrogen and methyl; and
$R^6$ is a 3-7 membered saturated ring containing one O heteroatom, wherein said 3-7 membered saturated ring is substituted with a substituent selected from the group consisting of hydrogen, $CF_3$ and methyl.

\* \* \* \* \*